(12) United States Patent
Reiner

(10) Patent No.: US 9,330,454 B2
(45) Date of Patent: May 3, 2016

(54) METHOD AND APPARATUS FOR IMAGE-CENTRIC STANDARDIZED TOOL FOR QUALITY ASSURANCE ANALYSIS IN MEDICAL IMAGING

(71) Applicant: Bruce Reiner, Berlin, MD (US)

(72) Inventor: Bruce Reiner, Berlin, MD (US)

( * ) Notice: Subject to any disclaimer, the term of this patent is extended or adjusted under 35 U.S.C. 154(b) by 310 days.

(21) Appl. No.: 14/025,345

(22) Filed: Sep. 12, 2013

(65) Prior Publication Data

US 2014/0072192 A1 Mar. 13, 2014

Related U.S. Application Data

(60) Provisional application No. 61/743,789, filed on Sep. 12, 2012.

(51) Int. Cl.
*G06K 9/00* (2006.01)
*G06T 7/00* (2006.01)
*G06F 19/00* (2011.01)

(52) U.S. Cl.
CPC ............ *G06T 7/0012* (2013.01); *G06F 19/321* (2013.01); *G06F 19/327* (2013.01)

(58) Field of Classification Search
None
See application file for complete search history.

(56) References Cited

U.S. PATENT DOCUMENTS

| 2007/0232868 | A1* | 10/2007 | Reiner | 600/300 |
| 2007/0237378 | A1* | 10/2007 | Reiner | 382/128 |
| 2009/0018867 | A1* | 1/2009 | Reiner | 705/2 |

* cited by examiner

*Primary Examiner* — Atiba O Fitzpatrick
(74) *Attorney, Agent, or Firm* — Jean C. Edwards, Esq.; Edwards Neils PLLC

(57) ABSTRACT

The present invention relates to a computer-implemented method of performing image quality analysis on images from an imaging examination, including: displaying an imaging examination; performing a quality review of the images; performing a quality analysis on data from the imaging examination and on the images; receiving image quality analysis from the user on the data and the images and storing the image quality analysis in at least one database; saving data from the image quality analysis on at least one key image of the images, using computer-generated standardized annotation and mark-up, or graphical data input, or speech data, using a computerized tool, and saving the data as annotated image data in the at least one database; and transferring the annotated image data to at least one quality assurance database with linking to images from the imaging examination.

38 Claims, 9 Drawing Sheets

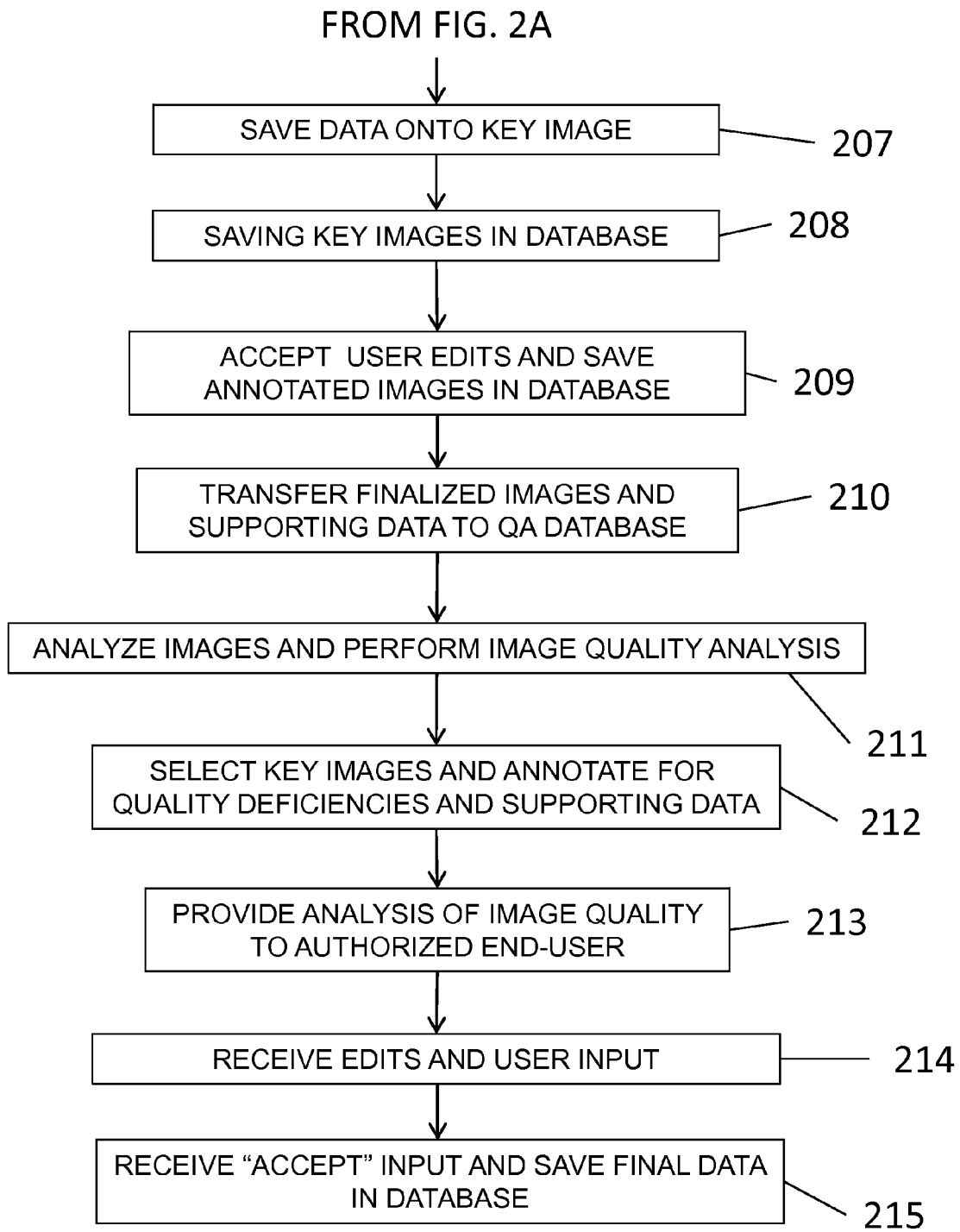

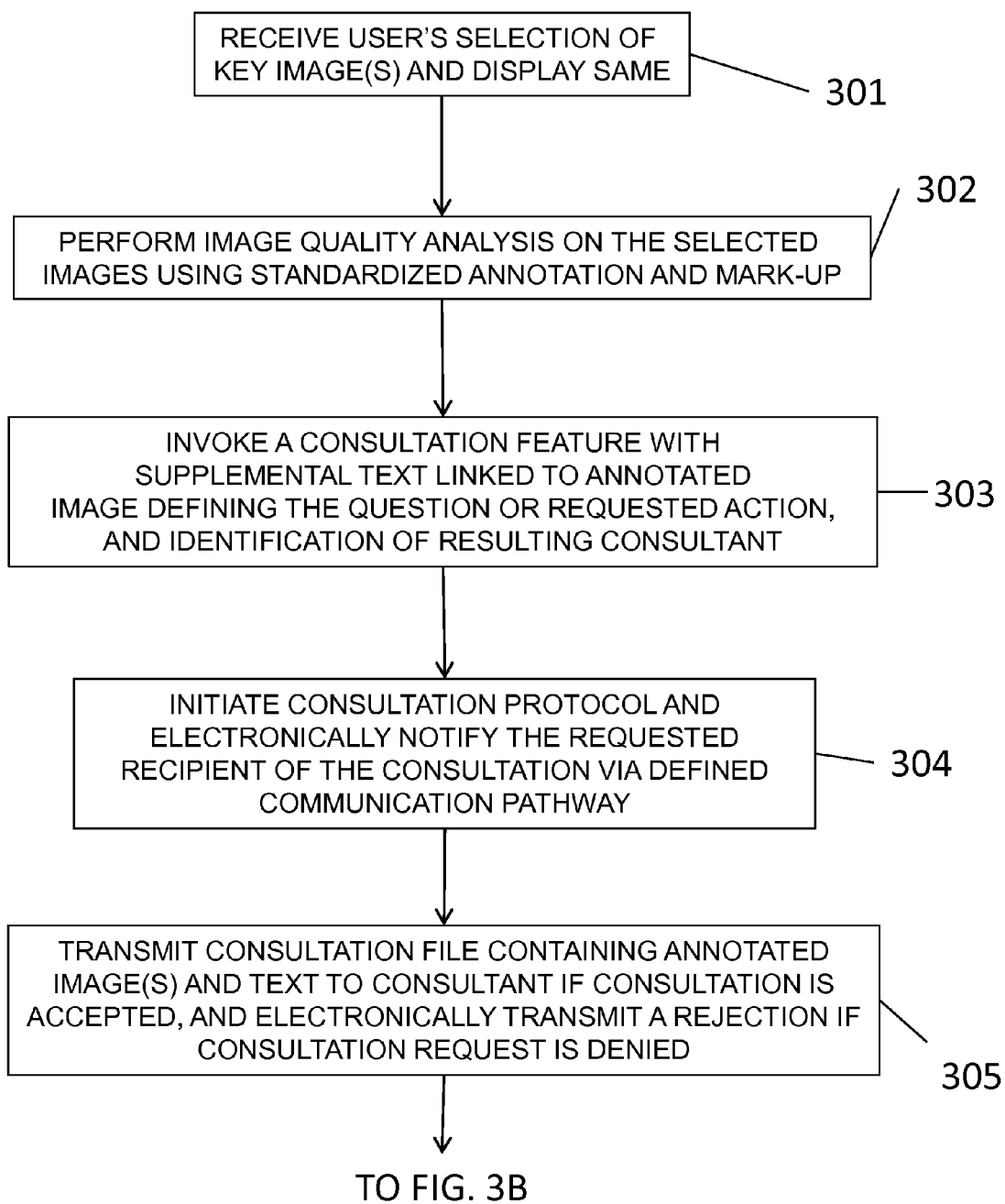

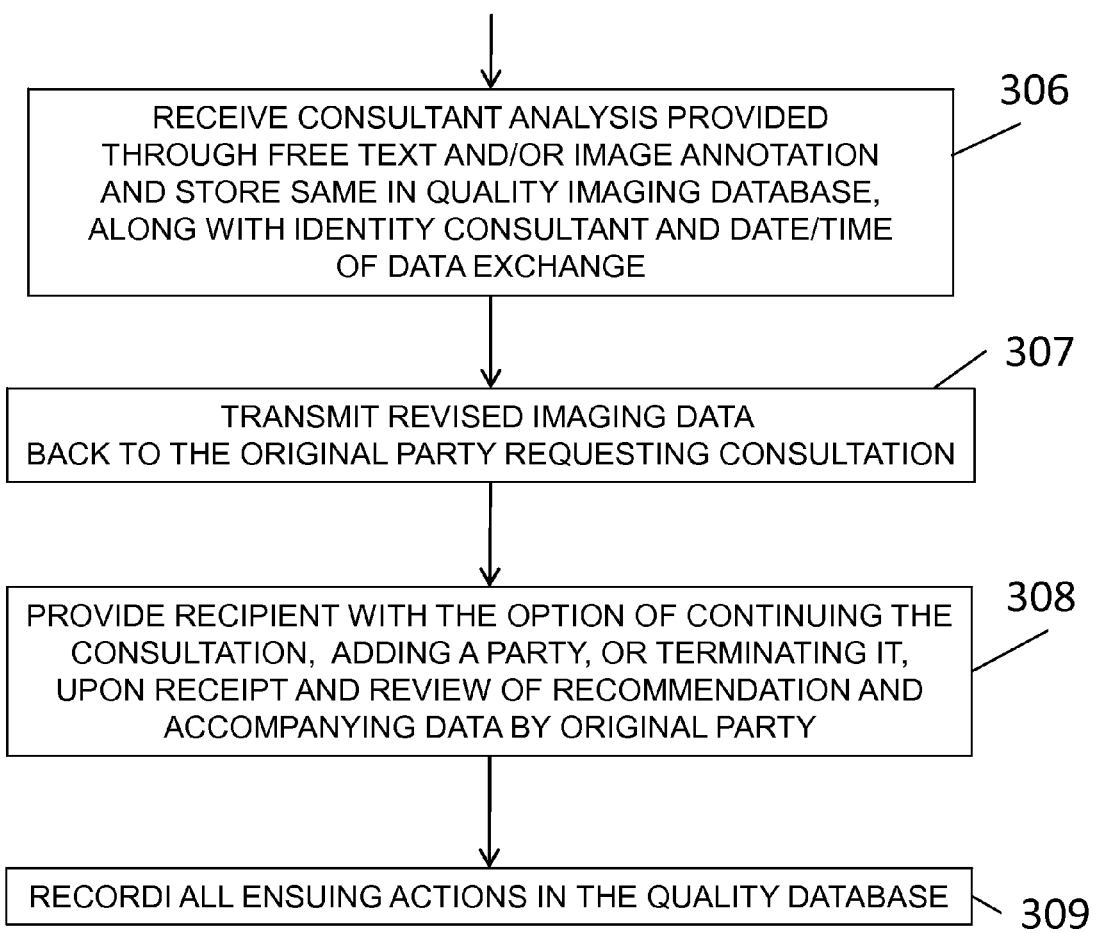

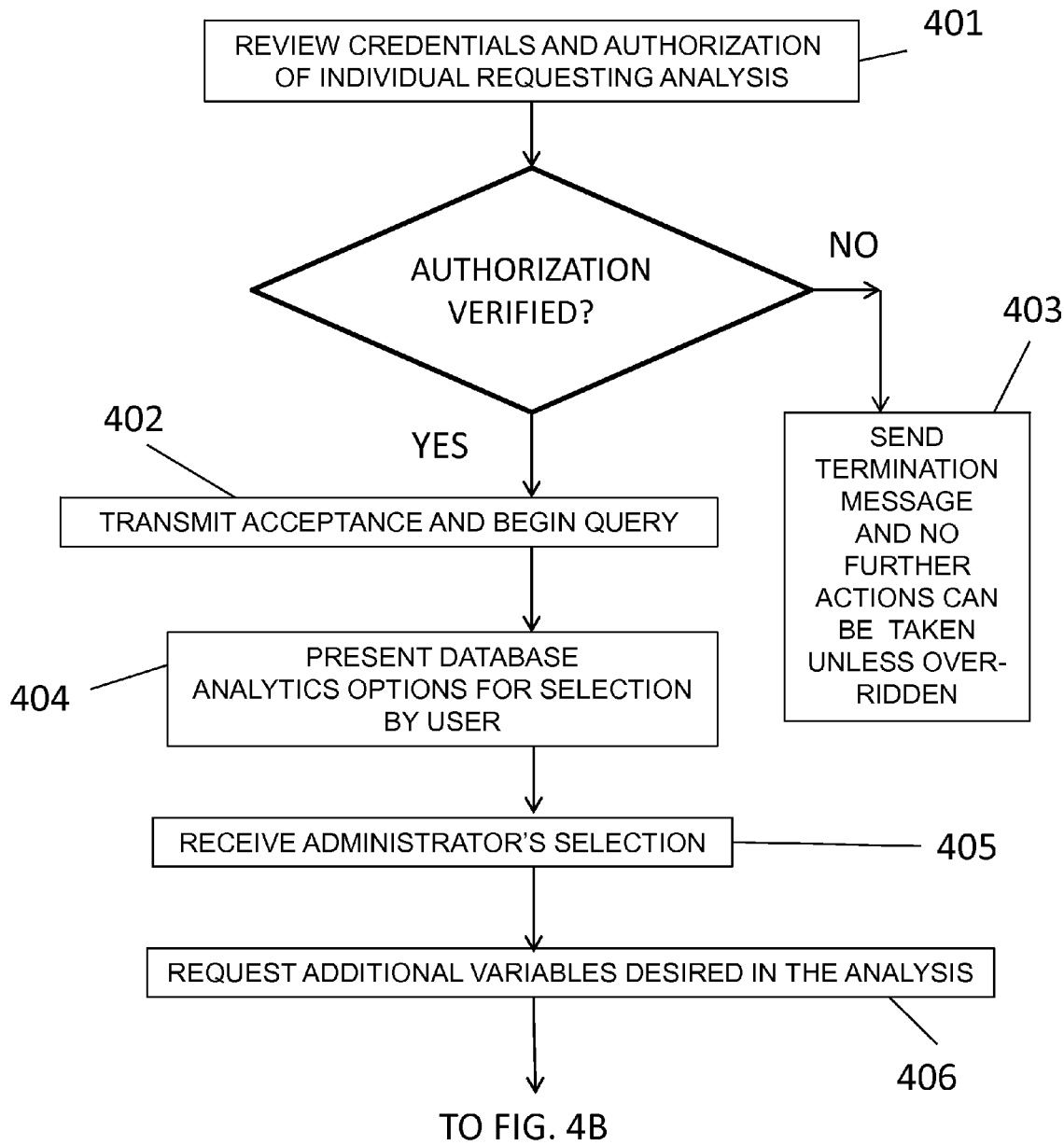

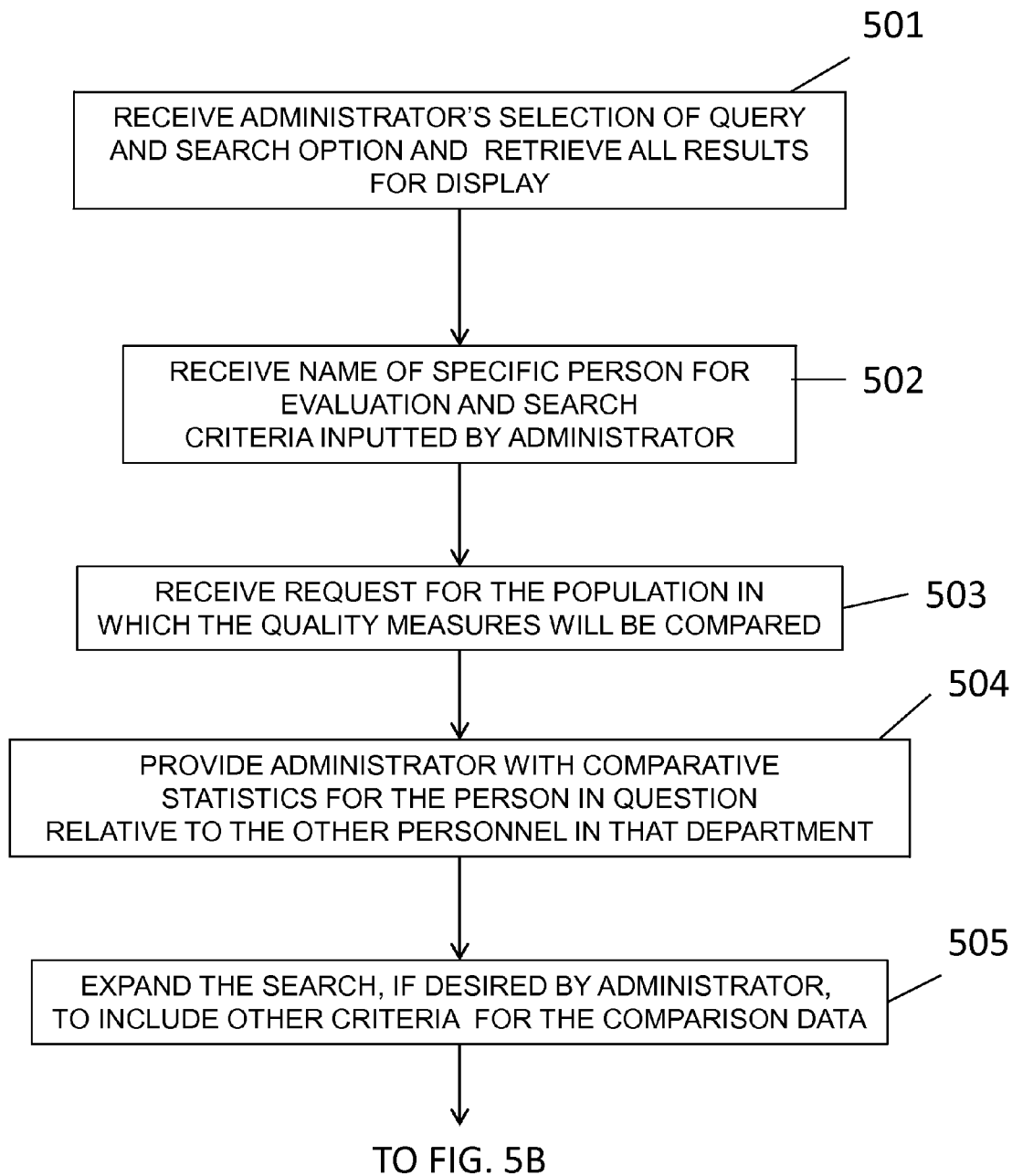

METHOD AND APPARATUS FOR IMAGE-CENTRIC STANDARDIZED TOOL FOR QUALITY ASSURANCE ANALYSIS IN MEDICAL IMAGING

CROSS-REFERENCE TO RELATED APPLICATIONS

The present application claims priority from U.S. Provisional Patent Application No. 61/743,789, filed Sep. 12, 2012, the contents of which are herein incorporated by reference in its entirety.

BACKGROUND OF THE INVENTION

1. Field of the Invention

The present invention relates a method and apparatus to improve medical imaging by standardizing image quality analysis, which directly links the quality data with the imaging dataset (i.e. image-centric), continuously tracks and records image quality data for longitudinal analysis, and analyzes all imaging datasets while taking into account a myriad of clinical, technical, and patient-specific variables affecting quality measures.

2. Description of the Related Art

In current medical practice, assessment of quality is highly subjective and personalized, personifying the old adage "beauty (i.e., quality) is in the eyes of the beholder". While almost all healthcare participants view quality as a high priority, standardized methods for quantitative and qualitative quality assessment are essentially non-existent. This lack of standardization in medical quality assessment produces an environment where quality deliverables are often left to the discretion of individual healthcare providers, who at the same time are being challenged to maintain revenue and profitability in an environment of declining economic reimbursements.

The net result is that quality often becomes sacrificed (or subservient) to concerns over productivity and workflow. In the absence of standardized quality metrics and tools for analysis, quality deliverables in healthcare will continue to stagnate (and potentially deteriorate), with the potential for adverse clinical outcomes and economic inefficiency.

Further, while all medical disciplines are affected to some degree by the relative lack of objective standards and methods of analysis, medical imaging is perhaps more prone to deficiencies and variation in quality due to its dependence on imaging (i.e., pictorial) data, as opposed to clinical (i.e., numerical) data. What one imaging provider (e.g., technologist, radiologist, administrator) may view as a "high quality" imaging dataset, another provider may view the same imaging dataset as possessing marginal or even poor quality. In the absence of an objective methodology to analyze image quality, the net result is that quality assessment in everyday practice remains somewhat elusive and undefined. This creates an environment where quality assessment is no longer focused on the imaging dataset (and the inherent diagnostic information derived from it), but instead on operational efficiency metrics (e.g., scheduling, report turnaround, and patient waiting times) which is easily measured and defined in numerical terms. As a result, many consumers of medical imaging services (e.g., referring clinicians, patients, third party payers) currently evaluate quality in these easily defined operational efficiency measures and largely ignore the intrinsic "clinical" quality of the imaging dataset, which ultimately determines the ability to render an accurate and reproducible diagnosis.

In medical imaging, image quality assessment can be performed internally or externally. Internal image quality assessment is typically performed by the technologist performing image acquisition, which usually includes a cursory review of the imaging dataset upon completion. This process is almost always "off the record" and results in no recorded data for longitudinal analysis. If an image quality deficiency is identified, the technologist makes a decision to allow the imaging dataset to be accepted "as-is", or elects to repeat the exam in part or in total, depending upon the exam type and severity of the deficiency. Unfortunately, in the current practice environment, productivity often tends to supersede quality, and as a result many imaging exams lacking in quality are accepted "as-is".

While the interpreting radiologist in theory serves as a "second line of defense" in maintaining quality standards, there is little incentive for the radiologist to override the decision of the technologist once the exam has been completed, the patient has left the department, and the imaging dataset has been transmitted to the imaging archive for interpretation. In the event that the radiologist perceived a significant quality deficiency warranting repeating of the imaging exam prior to interpretation, the patient would have to be recalled and the exam repeated. This has the undesired effect of increased radiation, reducing patient throughput, creating a backlog in the queue, and delaying diagnosis. As a result of these negative pressures, many imaging service providers tend to "make do" and accept image quality deficiencies, which in turn has the potential to result in equivocal or erroneous diagnoses, additional follow-up imaging exams, and additional consultations. Even in those relatively rare situations where a quality deficiency has resulted in an intervention (i.e., repeat exam or additional images), there is rarely any documentation recorded as to the specific nature and severity of the quality deficiency or involved portions of the imaging dataset. This results in incomplete imaging records, lack of traceable quality data, and lost educational opportunities.

External image quality assessment typically takes place when an imaging service provider is going through an accreditation process, which is customarily required for reimbursement by third parties. In this scenario, the medical imaging provider is typically asked to provide their operating procedures for review, along with a number of representative medical images from the modalities being evaluated for accreditation. Since the goal is aimed at passing the review process with the minimal amount of effort and scrutiny, the provider seeks out images of the highest quality. In doing so however, the broad spectrum of images is never really evaluated and this can mask existing quality deficiencies. The educational opportunity for critical review is replaced by a static and binary process of pass/fail. Once the accreditation process has been successfully completed, the provider often returns to "business as usual", repeating the same mistakes and quality imperfections as before the accreditation/review process took place. Since this accreditation/review process only takes place every 3-4 years, there is little incentive to critically review quality deliverables on a regular basis. The end result is that quality assessment in its current form is inherently flawed, performed in a piecemeal fashion, devoid of data, and lacks documentation.

While the current practice environment in quality assessment is flawed, it does create an opportunity for tremendous improvement. The key is to evaluate the existing practice deficiencies and create strategies and technologies which counteract and improve upon existing loopholes and gaps in medical imaging assessment.

Thus, a desired solution lies in creating objective and reproducible quality standards which can analyze the various steps and processes, players, and technologies in the healthcare continuum, with the goal of using this data to determine best practice guidelines and provide economic incentives to reward high-quality providers.

SUMMARY OF THE INVENTION

The present invention improves medical imaging by standardizing image quality analysis, directly links the quality data with the imaging dataset (i.e. image-centric), continuously tracks and records image quality data for longitudinal analysis, and analyzes all imaging datasets while taking into account a myriad of clinical, technical, and patient-specific variables affecting quality measures.

In one embodiment, the computer-implemented method of performing image quality analysis of a plurality of images from an imaging examination, includes: displaying an imaging examination selected by a user, on a display of a computer system; performing a quality review of the plurality of images from the imaging examination, using a processor of a computer system; performing a quality analysis on data from the imaging examination and on the plurality of images using the processor; receiving image quality analysis from the user on the data and the plurality of images and storing the image quality analysis in at least one database of the computer system; saving data from the image quality analysis on at least one key image of the plurality of images, using computer-generated standardized annotation and mark-up, or graphical data input, or speech data, using a computerized tool of the computer system, and saving the data as annotated image data in the at least one database; and transferring, using the processor, the annotated image data to at least one quality assurance database with linking to the plurality of images from the imaging examination.

In one embodiment, the method further includes authenticating the user using biometrics.

In one embodiment, the method further includes: receiving any quality analysis information inputted by the user on the plurality of images, in the quality review, to the at least one database.

In one embodiment, the user can review the annotated image data and can edit the annotated data prior to the processor transferring the saved annotated images to the at least one database.

In one embodiment, an image quality analysis is performed on the saved annotated image data by the processor.

In one embodiment, the key images are selected and annotated for quality deficiencies and supporting data by the processor, based on the image quality analysis performed on the annotated image data.

In one embodiment, the method further includes: providing an analysis of image quality on the annotated image data, performed by the processor, to an authorized user for review.

In one embodiment, the authorized user edits the image quality analysis on the annotated image data, and the processor receives the authorized user's input to one of Accept as-is, Modify, or Reject the edits.

In one embodiment, on condition that an Accept as-is input is received by the processor, the edited image quality analysis with the annotated image data and supporting data, is saved in the at least one database.

In one embodiment, the method further includes: initiating a consultation request with supplemental text linked to at least one annotated image in the annotated image data, defining a question or requested action, and identification of a consultant.

In one embodiment, the method further includes: notifying the consultant via electronic means of the consultation request; and forwarding a consultation file containing the annotated image and text to the consultant when the consultant accepts the consultation request.

In one embodiment, the method further includes: receiving a completed consultation from the consultant, with analysis and a revised annotated image from the consultant, and an identity of the consultant.

In one embodiment, the user has an option of continuing consultation with the consultant or an additional party or terminating consultation with the consultant.

In one embodiment, the method further includes: recording all actions with the consultant in the at least one database.

In one embodiment, the method further includes: providing database analytics, including a comparative analysis of quality data, to the user in ranked order.

In one embodiment, the method further includes: providing comparative statistics to the user on personnel, and importing the comparative statistics into performance evaluations of the personnel, along with any supporting data.

In one embodiment, the method further includes: devising a plan for targeted improvement and continued education of the personnel, along with salary changes commensurate with personnel quality performance data.

In one embodiment, when target or continued education dates for remedial action are not met by the personnel, steps are taken to relieve the personnel of access to appropriate medical or Quality systems.

In one embodiment, a computer system performs image quality analysis of a plurality of images from an imaging examination, and includes: at least one memory containing at least one program including the steps of: displaying an imaging examination selected by a user, on a display of a computer system; performing a quality review of the plurality of images from the imaging examination, using a processor of a computer system; performing a quality analysis on data from the imaging examination and on the plurality of images using the processor; receiving image quality analysis from the user on the data and the plurality of images and storing the image quality analysis in at least one database of the computer system; saving data from the image quality analysis on at least one key image of the plurality of images, using computer-generated standardized annotation and mark-up, or graphical data input, or speech data, using a computerized tool of the computer system, and saving the data as annotated image data in the at least one database; and transferring, using the processor, the annotated image data to at least one quality assurance database with linking to the plurality of images from the imaging examination; and at least one processor for executing the program.

In one embodiment, a computer-readable medium whose contents cause a computer system to perform image quality analysis of a plurality of images from an imaging examination, and the program includes the steps of: displaying an imaging examination selected by a user, on a display of a computer system; performing a quality review of the plurality of images from the imaging examination, using a processor of a computer system; performing a quality analysis on data from the imaging examination and on the plurality of images using the processor; receiving image quality analysis from the user on the data and the plurality of images and storing the image quality analysis in at least one database of the computer system; saving data from the image quality analysis on at least one key image of the plurality of images, using computer-generated standardized annotation and mark-up, or graphical data input, or speech data, using a computerized tool of the computer system, and saving the data as annotated image data in the at least one database; and transferring, using the processor, the annotated image data to at least one quality assurance database with linking to the plurality of images from the imaging examination.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

FIGS. 2A and 2B are a flowchart showing the steps of performing a quality review of images of an imaging examination, according to one embodiment consistent with the present invention.

FIGS. 3A and 3B are a flowchart showing the steps of utilizing a consultation request, according to one embodiment consistent with the present invention.

FIGS. 4A and 4B are a flowchart showing the steps of utilizing the data analytics feature, according to one embodiment consistent with the present invention.

FIGS. 5A and 5B are a flowchart showing the steps of performing personnel performance assessments, according to one embodiment consistent with the present invention.

DESCRIPTION OF THE INVENTION

The present invention improves medical imaging by standardizing image quality analysis, directly links the quality data with the imaging dataset (i.e., image-centric), continuously tracks and records image quality data for longitudinal analysis, and analyzes all imaging datasets while taking into account a myriad of clinical, technical, and patient-specific variables affecting quality measures.

Figure 1:
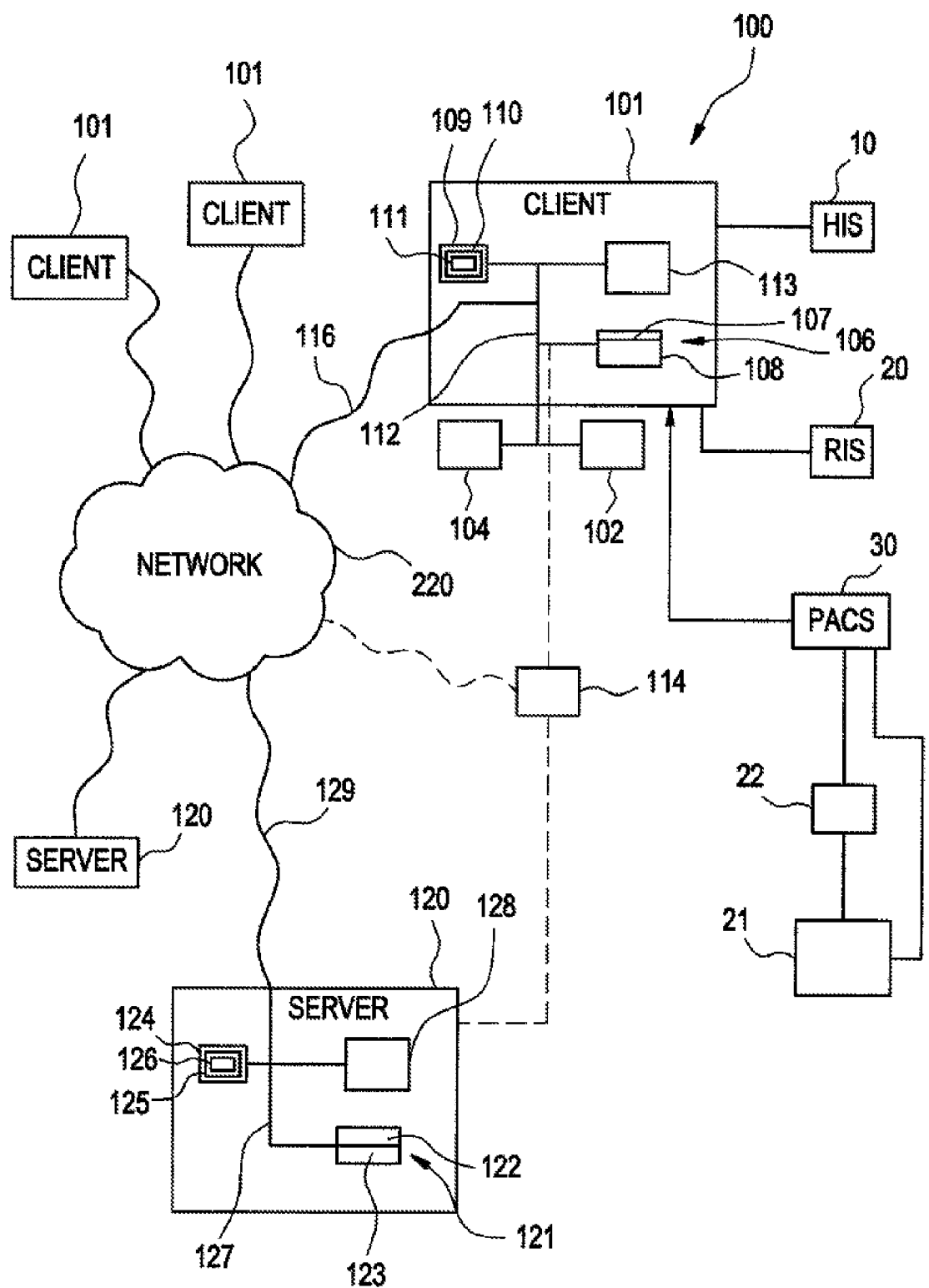
FIG. 1 shows a schematic diagram of a computer system, according to one embodiment consistent with the present invention.

According to one embodiment of the invention illustrated in FIG. 1, medical (radiological) applications may be implemented using the system 100. The system 100 is designed to interface with existing information systems such as a Hospital Information System (HIS) 10, a Radiology Information System (RIS) 20, a radiographic device 21, and/or other information systems that may access a computed radiography (CR) cassette or direct radiography (DR) system, a CR/DR plate reader 22, a Picture Archiving and Communication System (PACS) 30, and/or other systems. The system 100 may be designed to conform with the relevant standards, such as the Digital Imaging and Communications in Medicine (DICOM) standard, DICOM Structured Reporting (SR) standard, and/or the Radiological Society of North America's Integrating the Healthcare Enterprise (IHE) initiative, among other standards.

According to one embodiment, bi-directional communication between the system 100 of the present invention and the information systems, such as the HIS 10, RIS 20, QA sensor device 21, CR/DR plate reader 22, and PACS 30, etc., may be enabled to allow the system 100 to retrieve and/or provide information from/to these systems. According to one embodiment of the invention, bi-directional communication between the system 100 of the present invention and the information systems allows the system 100 to update information that is stored on the information systems. According to one embodiment of the invention, bi-directional communication between the system 100 of the present invention and the information systems allows the system 100 to generate desired reports and/or other information.

The system 100 of the present invention includes a client computer 101, such as a personal computer (PC), which may or may not be interfaced or integrated with the PACS 30. The client computer 101 may include an imaging display device 102 that is capable of providing high resolution digital images in 2-D or 3-D, for example. According to one embodiment of the invention, the client computer 101 may be a mobile terminal if the image resolution is sufficiently high. Mobile terminals may include mobile computing devices, a mobile data organizer (PDA), or other mobile terminals that are operated by the user accessing the program 110 remotely.

According to one embodiment of the invention, an input device 104 or other selection device, may be provided to select hot clickable icons, selection buttons, and/or other selectors that may be displayed in a user interface using a menu, a dialog box, a roll-down window, or other user interface. The user interface may be displayed on the client computer 101. According to one embodiment of the invention, users may input commands to a user interface through a programmable stylus, keyboard, mouse, speech processing device, laser pointer, touch screen, or other input device 104.

According to one embodiment of the invention, the input or other selection device 104 may be implemented by a dedicated piece of hardware or its functions may be executed by code instructions that are executed on the client processor 106. For example, the input or other selection device 104 may be implemented using the imaging display device 102 to display the selection window with a stylus or keyboard for entering a selection.

According to another embodiment of the invention, symbols and/or icons may be entered and/or selected using an input device 104, such as a multi-functional programmable stylus. The multi-functional programmable stylus may be used to draw symbols onto the image and may be used to accomplish other tasks that are intrinsic to the image display, navigation, interpretation, and reporting processes, as described in U.S. Pat. No. 8,081,165, the entire contents of which are hereby incorporated by reference. The multi-functional programmable stylus may provide superior functionality compared to traditional computer keyboard or mouse input devices. According to one embodiment of the invention, the multi-functional programmable stylus also may provide superior functionality within the PACS and Electronic Medical Report (EMR).

According to one embodiment of the invention, the client computer 101 may include a processor 106 that provides client data processing. According to one embodiment of the invention, the processor 106 may include a central processing unit (CPU) 107, a parallel processor, an input/output (I/O) interface 108, a memory 109 with a program 110 having a data structure 111, and/or other components. According to one embodiment of the invention, the components all may be connected by a bus 112. Further, the client computer 101 may include the input device 104, the image display device 102, and one or more secondary storage devices 113. According to one embodiment of the invention, the bus 112 may be internal to the client computer 101 and may include an adapter that enables interfacing with a keyboard or other input device 104. Alternatively, the bus 112 may be located external to the client computer 101. According to one embodiment of the invention, the image display device 102 may be a high resolution touch screen computer monitor. According to one embodiment of the invention, the image display device 102 may clearly, easily and accurately display images, such as x-rays, and/or other images. Alternatively, the image display device 102 may be implemented using other touch sensitive devices including tablet personal computers, pocket personal computers, plasma screens, among other touch sensitive devices. The touch sensitive devices may include a pressure sensitive screen that is responsive to input from the input device 104, such as a stylus, that may be used to write/draw directly onto the image display device 102.

According to another embodiment of the invention, high resolution goggles may be used as a graphical display to provide end users with the ability to review images. According to another embodiment of the invention, the high resolution goggles may provide graphical display without imposing physical constraints of an external computer.

According to another embodiment, the invention may be implemented by an application that resides on the client computer 101, wherein the client application may be written to run on existing computer operating systems. Users may interact with the application through a graphical user interface. The client application may be ported to other personal computer (PC) software, personal digital assistants (PDAs), cell phones, and/or any other digital device that includes a graphical user interface and appropriate storage capability.

According to one embodiment of the invention, the processor 106 may be internal or external to the client computer 101. According to one embodiment of the invention, the processor 106 may execute a program 110 that is configured to perform predetermined operations. According to one embodiment of the invention, the processor 106 may access the memory 109 in which may be stored at least one sequence of code instructions that may include the program 110 and the data structure 111 for performing predetermined operations. The memory 109 and the program 110 may be located within the client computer 101 or external thereto.

While the system of the present invention may be described as performing certain functions, one of ordinary skill in the art will readily understand that the program 110 may perform the function rather than the entity of the system itself.

According to one embodiment of the invention, the program 110 that runs the system 100 may include separate programs 110 having code that performs desired operations. According to one embodiment of the invention, the program 110 that runs the system 100 may include a plurality of modules that perform sub-operations of an operation, or may be part of a single module of a larger program 110 that provides the operation.

According to one embodiment of the invention, the processor 106 may be adapted to access and/or execute a plurality of programs 110 that correspond to a plurality of operations. Operations rendered by the program 110 may include, for example, supporting the user interface, providing communication capabilities, performing data mining functions, performing e-mail operations, and/or performing other operations.

According to one embodiment of the invention, the data structure 111 may include a plurality of entries. According to one embodiment of the invention, each entry may include at least a first storage area, or header, that stores the databases or libraries of the image files, for example.

According to one embodiment of the invention, the storage device 113 may store at least one data file, such as image files, text files, data files, audio files, video files, among other file types. According to one embodiment of the invention, the data storage device 113 may include a database, such as a centralized database and/or a distributed database that are connected via a network. According to one embodiment of the invention, the databases may be computer searchable databases. According to one embodiment of the invention, the databases may be relational databases. The data storage device 113 may be coupled to the server 120 and/or the client computer 101, either directly or indirectly through a communication network, such as a LAN, WAN, and/or other networks. The data storage device 113 may be an internal storage device. According to one embodiment of the invention, system 100 may include an external storage device 114. According to one embodiment of the invention, data may be received via a network and directly processed.

According to one embodiment of the invention, the client computer 101 may be coupled to other client computers 101 or servers 120. According to one embodiment of the invention, the client computer 101 may access administration systems, billing systems and/or other systems, via a communication link 116. According to one embodiment of the invention, the communication link 116 may include a wired and/or wireless communication link, a switched circuit communication link, or may include a network of data processing devices such as a LAN, WAN, the Internet, or combinations thereof. According to one embodiment of the invention, the communication link 116 may couple e-mail systems, fax systems, telephone systems, wireless communications systems such as pagers and cell phones, wireless PDA's and other communication systems.

According to one embodiment of the invention, the communication link 116 may be an adapter unit that is capable of executing various communication protocols in order to establish and maintain communication with the server 120, for example. According to one embodiment of the invention, the communication link 116 may be implemented using a specialized piece of hardware or may be implemented using a general CPU that executes instructions from program 110. According to one embodiment of the invention, the communication link 116 may be at least partially included in the processor 106 that executes instructions from program 110. According to one embodiment of the invention, if the server 120 is provided in a centralized environment, the server 120 may include a processor 121 having a CPU 122 or parallel processor, which may be a server data processing device and an I/O interface 123. Alternatively, a distributed CPU 122 may be provided that includes a plurality of individual processors 121, which may be located on one or more machines.

According to one embodiment of the invention, the processor 121 may be a general data processing unit and may include a data processing unit with large resources (i.e., high processing capabilities and a large memory for storing large amounts of data).

According to one embodiment of the invention, the server 120 also may include a memory 124 having a program 125 that includes a data structure 126, wherein the memory 124 and the associated components all may be connected through bus 127. If the server 120 is implemented by a distributed system, the bus 127 or similar connection line may be implemented using external connections. The server processor 121 may have access to a storage device 128 for storing preferably large numbers of programs 110 for providing various operations to the users.

According to one embodiment of the invention, the data structure 126 may include a plurality of entries, wherein the entries include at least a first storage area that stores image files. Alternatively, the data structure 126 may include entries that are associated with other stored information as one of ordinary skill in the art would appreciate.

According to one embodiment of the invention, the server 120 may include a single unit or may include a distributed system having a plurality of servers 120 or data processing units. The server(s) 120 may be shared by multiple users in direct or indirect connection to each other. The server(s) 120 may be coupled to a communication link 129 that is preferably adapted to communicate with a plurality of client computers 101.

According to one embodiment, the present invention may be implemented using software applications that reside in a client and/or server environment. According to another embodiment, the present invention may be implemented using software applications that reside in a distributed system over a computerized network and across a number of client computer systems. Thus, in the present invention, a particular operation may be performed either at the client computer 101, the server 120, or both.

According to one embodiment of the invention, in a client-server environment, at least one client and at least one server are each coupled to a network 220, such as a Local Area Network (LAN), Wide Area Network (WAN), and/or the Internet, over a communication link 116, 129. Further, even though the systems corresponding to the HIS 10, the RIS 20, the radiographic device 21, the CR/DR reader 22, and the PACS 30 (if separate) are shown as directly coupled to the client computer 101, it is known that these systems may be indirectly coupled to the client over a LAN, WAN, the Internet, and/or other network via communication links. According to one embodiment of the invention, users may access the various information sources through secure and/or non-secure internet connectivity. Thus, operations consistent with the present invention may be carried out at the client computer 101, at the server 120, or both. The server 120, if used, may be accessible by the client computer 101 over the Internet, for example, using a browser application or other interface.

According to one embodiment of the invention, the client computer 101 may enable communications via a wireless service connection. The server 120 may include communications with network/security features, via a wireless server, which connects to, for example, voice recognition. According to one embodiment, user interfaces may be provided that support several interfaces including display screens, voice recognition systems, speakers, microphones, input buttons, and/or other interfaces. According to one embodiment of the invention, select functions may be implemented through the client computer 101 by positioning the input device 104 over selected icons. According to another embodiment of the invention, select functions may be implemented through the client computer 101 using a voice recognition system to enable hands-free operation. One of ordinary skill in the art will recognize that other user interfaces may be provided.

According to another embodiment of the invention, the client computer 101 may be a basic system and the server 120 may include all of the components that are necessary to support the software platform. Further, the present client-server system may be arranged such that the client computer 101 may operate independently of the server 120, but the server 120 may be optionally connected. In the former situation, additional modules may be connected to the client computer 101. In another embodiment consistent with the present invention, the client computer 101 and server 120 may be disposed in one system, rather being separated into two systems.

Although the above physical architecture has been described as client-side or server-side components, one of ordinary skill in the art will appreciate that the components of the physical architecture may be located in either client or server, or in a distributed environment. Further, although the above-described features and processing operations may be realized by dedicated hardware, or may be realized as programs having code instructions that are executed on data processing units, it is further possible that parts of the above sequence of operations may be carried out in hardware, whereas other of the above processing operations may be carried out using software.

The underlying technology allows for replication to various other sites. Each new site may maintain communication with its neighbors so that in the event of a catastrophic failure, one or more servers 120 may continue to keep the applications running, and allow the system to load-balance the application geographically as required.

Further, although aspects of one implementation of the invention are described as being stored in memory, one of ordinary skill in the art will appreciate that all or part of the invention may be stored on or read from other computer-readable media, such as secondary storage devices, like hard disks, floppy disks, CD-ROM, or other forms of ROM or RAM either currently known or later developed. Further, although specific components of the system have been described, one skilled in the art will appreciate that the system suitable for use with the methods and systems of the present invention may contain additional or different components.

The present invention provides a methodology for image quality analysis in which the images themselves are used to rate image quality, characterize specific quality deficiencies, and record the data in a standardized manner. Since image quality analysis is intrinsically tied to the image itself, the present invention relies on the program 110 recording the representative image or images with corresponding descriptive data, in the database, in graphical, numerical, and/or textual formats. Both manual and computerized methods of quality analysis can be utilized by the program 110 for data input, using a standard methodology for image quality analysis, which in turn is recorded by the program 110 into a standardized and referenceable database. A number of data input options are supported by the present invention, including graphical image mark-up and annotation, textual data (which defines the specific image quality deficiency), and numerical data (which provide a standardized grading system for various quality metrics). A comprehensive image quality ontology supports all three methods of data input and provides a mapping of graphical, numerical, and textual data elements.

As an example, if an end-user was to save a chest CT image to identify excessive respiratory motion limiting image quality, he or she could record the data in the database by either annotation of the area of the image with motion, using either the motion artifact graphical icon or corresponding textual terminology, and along with the numerical grade for severity. The image would in turn, be recorded by the program 110 into the standardized image quality database with combined graphical (i.e., image annotations), textual, and numerical data elements. At the time of subsequent review, the image and corresponding standardized data elements would be presented on the display for review by the program 110, along with the defined region of interest.

The concept of creating reports using a standardized image mark-up and annotation system has been previously described in U.S. Pat. No. 7,421,647, the contents of which are herein incorporated by reference in its entirety. In U.S. Pat. No. 7,421,647, the interpreting radiologist creates the radiology report by using a standardized image annotation and mark-up system mapped to report findings. In the present invention, the same methodology is used to create an image quality report; but instead of using annotations to describe pathologic findings within the imaging dataset, the graphical annotations and image mark-up are used by the program 110 to describe image quality deficiencies and overall assessment of image quality. The corresponding data is then used by the program 110 to create two simultaneous versions of report data—i.e., in graphical and textual formats.

The resulting "image quality" data can be recorded by the program 110 in the database, and viewed on the display alone (i.e., image quality report), or combined with the "radiology report" data. In the combined version, the report would contain both radiologic findings (i.e., clinical abnormalities such as pneumonia) and image quality data. This would provide the added perspective of how the imaging data was used for clinical diagnosis, as well as the technical limitations in diagnosis due to image quality deficiencies.

As stated above, both manual and automated methods of image quality assessment can be used for analysis by the program 110. In the manual mode of operation, an end-user (e.g., technologist, radiologist, clinician) could input their image quality assessment data by selecting an image or images which best serves to illustrate their subjective image quality assessment, and annotate these saved images in accordance with the specific image quality deficiencies of concern along with subjective image quality ratings. Quality Assessment Variables include, but are not limited to: identifying information, exposure, positioning, spatial resolution, contrast resolution, radiation dose, noise, collimation, and artifacts.

The present invention would support multiple data input options including (but not limited to) speech, manual, and computer generated icons. Regardless of the input method used, the quality ontology of the program 110 would map the input data with corresponding graphical, textual, and numerical data, and combine all three forms of data into the saved image. At any time when these saved images are retrieved from the database and reviewed, all 3 data formats will be available on the display for review along with the corresponding annotated image/s.

In the automated method of image quality assessment, the program 110 performs image quality analysis by automatically recording detected image quality deficiencies, overall image quality ratings, and the corresponding images of interest in the database. Two examples of computerized methods for image quality analysis have been described in prior patents, such as U.S. Pat. Nos. 8,018,487, and 8,333,508, the contents of which are herein incorporated by reference in their entirety, and the contents of these patents could be applied as input methods for the present invention. The output data would be identical in both manual and automated forms of data input, and include selected images with corresponding standardized quality assessment data in graphical, textual, and numerical formats. The presentation mode of this data can be customized by the program 110 in accordance with each individual end-user's preferences and tied to their authentication/identification signature.

Once quality assessment data has been recorded by the program 110 in the database, it can be accepted "as-is" or subjected to an external verification process. This provides a mechanism for secondary data review and modification, if deemed appropriate. The data verification process can include a second quality assessment by an independent third party (using either automated or manual modes of operation), and can be performed either in a blinded fashion (i.e., without access or knowledge of prior image quality assessment data), or as an over-read having access to the original image quality assessment data. In the event that a significant discrepancy exists between the primary and secondary image quality assessments, a final arbitrator can be employed for reconciliation and finalization of image quality assessment.

In all scenarios, the review process should be performed in an anonymous fashion, so that image quality assessment is performed without knowledge of the patient, operator, institutional, technology, or reviewer identity. This provides a means with which information confidentiality is maintained and potential bias is alleviated.

The present invention provides the ability for multiple independent parties to input quality assessment data, with the ability to restrict what data is ultimately recorded and utilized in the final analysis. As an example, the technologist performing the image acquisition may elect to input their own image quality assessment, which in turn may or may not be used by the radiologist in his/her own image quality assessment. The technologist could simply save the image(s) of interest, annotate them accordingly, and provide an overall image quality score to the imaging dataset. At the time of data input, he/she may request additional feedback based upon third party evaluation (e.g., radiologist, supervisory technologist, QA specialist) and downstream data analytics. By doing so, the quality data associated with that specific exam will be automatically flagged by the program 110, and subsequent data will be transmitted by the program 110 to the technologist for future review. This provides educational opportunities for imaging personnel to gain valuable knowledge and perspective of how their individual performance is measured in overall quality, as well as educational opportunity aimed at better understanding and knowledge of image quality.

From the educational perspective, the technologist performing an imaging exam (e.g., chest CT) may observe an undetermined quality deficiency in the dataset, which he/she is unsure of as to the underlying etiology and clinical significance. Before allowing the patient to be discharged from the imaging department and lose the opportunity to modify the imaging dataset, the CT technologist may capture the image/s of interest, annotate the images and region of interest using either graphical mark-up or text, and save the images in the database for future reference.

At the time of image capture and annotation, the technologist can determine the desired function of the action to be taken. In addition to the option of "Image Quality Assessment", the program 110 would also provide the end-user (e.g., technologist, radiologist, administrator) with a number of other options including (but not limited to) Consultation, Database Query, Education/Teaching File, Research, Technology Assessment, and Clinical Outcomes Tracking.

In this specific example, the technologist wishes to invoke the Consultation feature and requests a real-time consultation of the radiologist assigned to CT interpretation on that given day. Since that radiologist may not be in immediate proximity to the CT Scanner (e.g., reading area physically separated from CT suite, off-site teleradiology, on-call coverage), the program 110 provides a mechanism for real-time consultation along with the ability to record and capture all data in the communication pathway in a standardized format.

In addition to selecting the option as to the desired action, the program 110 of the present invention also provides a hierarchical rating as to the degree of timeliness and clinical significance associated with the action. Since in this example, the technologist is holding up finalization of the imaging dataset and patient discharge, the consultation request is flagged by the program 110 as "Stat", which in turn triggers an escalation pathway with time stamps in the QA database. Upon receipt of the consultation request, the radiologist opens up the online QA folder (which contains the pertinent images, region of interest, standardized annotation data, and action requested). Upon reviewing the annotated images and supporting data (all of which is recorded in a standardized format), the radiologist responds to the consultation request by inputting the corresponding data directly onto the images of record using input means. In this example, the quality deficiency of concern may have been due to an artifact and require a repeat of the anatomic region of interest. The annotated image would now contain annotation data from the technologist (which initiated the consultation) and that of the radiologist (which provided an answer to the consultation along with recommendation as to how to proceed). The captured QA images can be recorded on an individual basis or collectively, in the database, in which both sets of annotation data (technologist and radiologist mark-ups) can be simultaneously displayed on the display, and time stamped.

While a number of display options can be used to illustrate different data sources and time, one easy method would be to use color coding to distinguish between the different data (e.g., technologist data displayed in red, radiologist data displayed in blue). In the event, that the corresponding QA data was reviewed at a later date, the viewer would have the option of filtering various data so that only the data of primary interest is displayed on the display. This creates an effective means with which sequential data of different sources can be preferentially reviewed in accordance with the individual preferences of the reviewer. While the viewer would have the option to "filter" and display the QA data in accordance with their own subjective preferences, all data recorded by the program 110 in the QA continuum would be recorded in the QA database, with identification of the author, location, and time of the event. This provides an easily traceable method for reviewing the various observations and actions which took place during the course of patient care.

An alternative method for education would be available in the form of a Database Query request. In this application, the technologist would perform the same functions (i.e., save the desired image/s, highlight the anatomic region of interest, and input annotation data); however, instead of requesting a consultation from the radiologist, in this scenario, the technologist would initiate a computerized search of the QA database in an attempt to identify other annotated images with similar QA deficiencies. Because the QA data is recorded and stored in the database in a standardized fashion, this provides an effective means with which QA images from multiple institutions can be combined and used for meta-analysis and search queries. The program 110 would search the QA database based upon terms such as the anatomic region (chest), modality (CT), and standardized annotation data recorded (artifact). The program 110 would then utilize artificial intelligence techniques to identify images of similar profiles which present a match, while rating (on a numerical scale) the similarity between the submitted QA images and those in the database of a similar appearance. The corresponding "matched QA images" would then be available for review by the technologist along with the supporting QA data (e.g., technology used, image acquisition parameters, specific QA deficiency, clinical significance, image quality score). This educational component of the present invention would therefore serve as a form of computerized decision support to support QA analysis at the point of care.

In an alternative embodiment, the imaging dataset submitted for interpretation may be deficient in terms of quality, and require further action as determined by the interpreting radiologist. In this scenario, the radiologist determines that the overall deficiency in image quality precludes accurate diagnosis, and additional and/or repeat imaging is required. The radiologist saves the image/s of interest in the database, annotates them in accordance with the region of interest, type of deficiency, and desired action (i.e., "follow-up action required"). Upon inputting the requested action of "Follow-up", the radiologist is then asked by the program 110 to specify the desired follow-up action to be taken (e.g., repeat imaging, image processing, additional clinical data). The resulting QA data including the annotated images and supporting data) would then be reviewed by a supervisory technologist, QA specialist, or administrator, to ensure that the requested action is justifiable and the necessary steps are taken to satisfactorily address the reported QA deficiency. In all cases, each step of the QA continuum is recorded in the QA database by the program 110, thereby providing a method for review and analysis in the event that an adverse outcome was to occur.

The corresponding data would also be recorded in a stakeholder-specific QA database by the program, which provides data related to quality metrics, education/training, and follow-up actions specific to each individual stakeholder. Similar QA database profiles and analyses are also created for individual technologies, thereby providing an objective measure for comparative technology assessment as it relates to quality measures.

The data obtained can also be used prospectively to optimize work distribution, in an attempt to maximize quality in accordance with historical quality analytics. As an example, a patient is scheduled for a CT colonography for colon cancer screening. The particular patient profile identifies a number of quality-related variables which places the patient at a "high difficulty" quality category (e.g., large patient size, poor mobility, prior history of non-compliance, respiratory insufficiency restricting breath holding, indwelling surgical hardware producing beam hardening artifact). This patient profile quality assessment can be performed at the time of order entry and exam scheduling, with an automated patient quality assessment score attached to the exam order. The methodology for creating this patient quality assessment score is similar to that described in U.S. patent application Ser. No. 12/137,926, filed Jun. 12, 2008 for the Productivity-Workflow Index (the contents of which are herein incorporated by reference in their entirety), and involves the creation of a list of patient-specific metrics which collectively impact the predicted ease or difficulty for imaging quality, relative to the specific exam being requested. Due to the fact that exam individual imaging exam (and anatomy being evaluated) has its own unique steps, requirements, and challenges; the program 110 derived patient quality assessment scores are unique for each patient, anatomic region of interest, exam type, and clinical indication.

Once the exam-specific patient quality assessment score is calculated (using computer algorithms) by the program 110, the corresponding score is attached to the order request. When the order is reviewed for scheduling, the human or computerized scheduler would match the specific exam type, date, and patient quality assessment score to the optimal technology and operator. This provides a proactive and quantitative tool for optimizing the interaction effects which exist between quality, patient, operator, and technology.

Three exemplary embodiments are provided for illustrative purposes. In the first example, a young and relatively healthy male is scheduled to undergo a screening chest CT for lung cancer. Based upon the patient's health status, clinical indication, exam type, and prior imaging history (i.e., image quality scores for that patient with a focus on CT), the patient quality assessment score is determined to be 9 out of a possible 10; indicating the expected quality of the exam to be performed is very high. This data is then correlated by the program 110 with the CT technologist schedule for the scheduled date of the exam. There are four CT technologists scheduled to work on the given day: one of whom is relatively new (i.e., inexperienced); two of whom are highly experienced with above average quality performance metrics for the exam of interest; and one of whom possesses significantly higher experience and quality scores. The last factor to be considered is the technology (i.e., CT scanner); of which there are three CT scanners operating on that day and site. Of these three CT scanners: one is brand new and possesses state of the art software; while the other 2 CT scanners are a bit older and differ in terms of their software packages and image processing capabilities. When all of these factors are considered, it is determined that the high patient quality assessment score and relatively low exam difficulty result in an exam considered to be of "low quality risk". As a result, the program 110 places scheduling restrictions on the assignment of the CT technologist and CT scanner.

In the second example, the same exam (i.e., chest CT) is being ordered for a different clinical indication (i.e., unexplained weight loss), and on an older and frail patient, who has a history of poor image quality scores. Based upon these data, the exam is considered to be of "intermediate quality risk", and as a result, the selection of the operator (i.e., technologist) and technology (i.e., CT scanner) take on greater importance. As a result, when the quality analysis is performed by the program 110, the scheduler elects to schedule the exam with a more experienced technologist, who has had prior experience with this particular patient and relatively good image quality scores. The choice of technology is of lesser importance because all three CT scanner options are deemed to be sufficient for the desired task.

In the third example, the exam and clinical indications are different (i.e., chest CT angiography for evaluation of pulmonary embolus), and as a result, present a greater technical challenge than the other two examples. In addition, the patient the exam is being ordered on is currently in the intensive care unit (ICU), due to complex medical problems which drastically limit patient mobility and compliance. These combined factors result in a pre-test patient quality assessment score of 2 out of a possible 10, and the exam is rated by the program 110 as "high quality risk".

As a result of these factors, it is determined that operator and technology selections are critical in maximizing quality for the requested exam. When the program 110 correlates with the four available CT technologists' quality analytics (i.e., technologist quality profile), it is determined that one specific technologist has far superior training and quality performance scores than their colleagues, so this specific technologist is selected by the program 110. (In actuality, that technologist had been previously assigned to another exam at the time and date of interest, but was reassigned based upon this higher priority assignment).

Lastly, of the three available CT scanners, the newer and more advanced scanner (in terms of software package and image processing capabilities) was selected by the program 110 due to the technical challenges associated with the exam type, clinical indication, and patient profile. These examples attempt to illustrate the dynamic use of image quality data and how it can be used prospectively as a tool for decision support, quality improvement, and enhanced operational efficiency.

The image quality database can also be used as a real-time decision support tool for protocol optimization. This application takes advantage of the fact that the image quality data associated with historical imaging exams (of a particular exam type, anatomic region, clinical indication, and patient) can be used by the program 110 to prospectively optimize image acquisition parameters for the purpose of improving quality and safety.

Three exemplary embodiments are provided for illustrative purposes:
1. Patient is scheduled for a follow-up abdomen CT for re-evaluation of liver cancer following chemotherapy.
2. An ICU patient is scheduled for a repeat portable chest radiograph following venous catheter placement.
3. A patient who has never been imaged before is now being scheduled for a lung cancer screening chest CT.

In the first example, the patient is being re-evaluated in a relatively short time interval for a known pathology (i.e., liver cancer) with an established baseline of anatomy and pathology. Since all that is really needed is a comparative assessment of tumor size following chemotherapy, the technical requirements for the exam are less than would be required for a "first time" CT exam. As a result, radiation dose reduction strategies can be employed by the program 110 to reduce radiation exposure (safety). At the same time, the previous CT exam's image quality assessment data can be used by the program 110 to optimize the current exam protocol.

As an example, suppose the prior CT image quality assessment by the program 110 determined that the contrast administration was sub-optimal (i.e., poor quality) due to the timing and rate of contrast administration. Review of the corresponding contrast-related technical data by the program 110 showed that the rate of contrast administration was limited by the size of the intravenous catheter used (i.e., 22 gauge catheter), and the timing of the contrast bolus was limited by an insufficient time delay between the time of contrast administration and initiation of image acquisition. Upon recognition of these two previous quality deficiencies by the program 110, the current exam protocol and catheter placement is modified by the program 110 (based upon either human or computer analysis of the prior image quality data), by increasing the time delay from 10 to 30 seconds and increasing the size of the intravenous catheter from 22 to 18 gauge. This illustrates how protocol optimization can be performed to improve quality and safety factors based upon analysis of the historical imaging database by the program 110.

In the second example, a repetitive imaging study is being performed on the same patient for a routine clinical indication. Once again, the patient's baseline status has been well established, due to the repetitive frequency of having multiple exams of the same type over the course of a few days. Based upon the clinical data, the exam is requested for the purposes of defining the location of the newly inserted venous catheter and to ensure no post-procedural complications have taken place. Upon review of the image quality database by the program 110, it is learned that the technique used for prior exams (portable chest radiographs) has been quite variable and resulted in far different quality assessment scores. By the program 110 using this historical image quality data, the current exam acquisition parameters can be best determined by the program 110 selecting those parameters associated with the highest quality image scores. In addition, a specialized post-image processing technique is available to the program 110 to improve the conspicuity of line detection. The combination of the program 110 using optimal exposure parameters (based upon historical image quality and technical data), and specialized image processing (in accordance with the clinical indication), provides a reliable method for simultaneously improving image quality and diagnosis.

In the third example, the patient does not have an historical imaging database for the program 110 to review for the purposes of image quality improvement. On the other hand, utilizing data from the patient profile, exam type, clinical indication, and technology profile, the program 110 can query the universal image quality database to assist with protocol optimization. Due to the fact that the image quality data is recorded in a standardized fashion and accounts for supporting data elements (e.g., patient profile, technology used, exam type, clinical indication), the universal (i.e., multi-institutional) database can be used by the program 110 for protocol optimization, despite the fact that no prior image quality data is available for this particular patient.

By correlating the patient quality assessment score with the exam type, clinical indication, and technology being used, the program 110 can provide complimentary image quality and protocol data from similar exams stored in the imaging databases. Depending upon the confidence of the match (related to the patient profile, technology in use, and clinical indication); the program 110 can present the corresponding technical parameters of comparable exams with the highest image quality scores.

The technologist performing the study has the option of inputting additional variables (e.g., radiation dose reduction, reduced contrast volume, faster scanning speed), for additional analysis, if desired. The goal is to proactively optimize quality (and safety), based upon statistical analysis of the image quality database.

The utilization of data from the patient-specific, technology-specific, and universal image quality databases by the program 110, can also create data-derived "best quality" guidelines, which are the basis for Evidence-Based Medicine (EBM). Meta-analysis by the program 110 of these databases provides an objective means with which researchers and professional societies can determine the most efficacious manner in which medical imaging can be used to maximize quality, cost-efficiency, and safety. This can be as passive as periodically released recommendations and societal standards for review, or as active as electronic alerts and notifications at the point of care when the image quality measures fall below acceptable standards. The application of these data-derived EBM guidelines can take place at the level of the individual operator (e.g., technologist, radiologist), department, or institution and be made available for access by medical imaging consumers (e.g., patients, referring clinicians, payers). This constitutes a portion of the data described in U.S. Pat. Nos. 7,933,782, 7,831,445, 7,532,942, 7,853,476, 8,301,461, and 8,538,776, and U.S. patent application Ser. No. 12/213,184, filed Jun. 16, 2008, the contents of which are herein incorporated by reference in their entirety.

As new societal standards and data-driven best practice guidelines are created and revised (which is a continuous process), the quality ontology and standardized image annotation and mark-up can be readily adapted by the program 110 to reflect these changes. If, for example, a new category of image quality deficiency is created by the program 110, this could be added to the ontology using standardized language, graphical annotation, and numerical grading to incorporate the new quality standards. Since image quality assessment, technology, and clinical practice is constantly changing; it is expected that the program 110 and associated ontology would concurrently modify to reflect these dynamic changes. The education and consultation features of the present invention provide an excellent means with which these changes in best practice guidelines can be communicated.

As an example, if optimal radiation dose reduction strategies for pediatric CT were to change, based upon new clinical research and/or technology development; it may be difficult for many medical imaging practitioners to constantly stay abreast of these changing recommendations. One effective way to accomplish this education/practice improvement goal would be for the program 110 to integrate these "best practice" recommendations into the universal QA database and decision support tools. As an example, when a pediatric patient is scheduled for a CT exam which has undergone a recent change in recommended protocol, an automated alert would be sent by the program 110 to all involved stakeholders (e.g., scheduler, technologist, radiologist, administrator, referring clinician) to notify them of the new quality standard and recommendations, acknowledge receipt and understanding of these changes, and integration of these modifications into the QA database decision support application. At the time when the patient is ready to undergo the CT exam and the technologist performing the study enters in the protocol and acquisition parameters, the program 110 would provide a prompt to the technologist reminding them of the changes and incorporate these into the computer-derived protocol recommendations.

As computerized decision support and analytical tools become more robust and ubiquitous in medical imaging practice, it would be expected that many human-derived decisions would begin to be replaced or enhanced by computerized intelligence and analysis. One example would be the process of evaluating and quantifying image quality. In its current form, this is almost exclusively performed by humans (e.g., technologist, QA specialist, radiologist) but could at some time, be performed using computerized algorithms. At that time, the invention would support data input in either or both forms, with the ability for the end-user to edit and/or modify the input data before final acceptance. The source of the data would be recorded in the database to provide a means for the program 110 to analyze inter and intra-observer variability.

The practice of quality assurance in medical imaging is currently mandated by accrediting organizations (e.g., JCAHO, ACR), and customarily includes a periodic review of imaging exams, technologies, and radiology reports to ensure compliance with established standards. Unfortunately, the current practice of QA is largely retrospective in nature, is internal (and therefore subject to a potential bias and conflict of interest) and often performed in a manner which fulfills the minimum expectations for certification, accreditation, or credentialing. By creating a standardized image quality database, and a program 110 which captures images and directly integrates quality-related data, the present invention creates a methodology for practicing QA in real-time, while providing for external and unbiased quality assessment.

A third party QA evaluator could in theory access the imaging database as medical imaging studies are being performed, analyze image quality using the standardized and image-embedded methodology of the program 110, and directly interact with the imaging staff at the point of care in the hopes of enhancing education, training, and clinical outcomes. By having the ability to randomly access images, the current QA model of provider pre-selected (and optimal) images would be supplanted by a model utilizing randomized imaging data selection which encompasses the full spectrum of patient profiles, technologies used, clinical data, exam types, and technical parameters. By the program 110 integrating image quality assessment data directly into the images, the opportunity for education/training, consultation, and intervention is accentuated in a timely fashion; obviating the need to access and review voluminous imaging datasets, and eliminating the potential to misappropriate image quality report data with the corresponding images.

Another important attribute of the present invention is the ability of the program 110 to customize data display presentation in accordance with the individual preferences of the individual stakeholder or institution. By standardizing image quality data, recording all instances of data review and input, and directly embedding this data into the corresponding images, the program 110 provides an easy-to-use method for displaying image quality data over the continuum of care. Image quality data may be recorded into the database by the program 110 at a variety of steps including (but not limited to), image acquisition (by the technologist), image interpretation (by the radiologist), and report review (by the referring clinician). The resulting image quality mark-up and annotation would therefore, entail multiple data inputs by different end-users over a sequential course of time. If the imaging dataset from a particular exam is subsequently reviewed at a later time (e.g., follow-up imaging exam, consultation, QA review); the reviewer would have the opportunity to display any combination of the image quality data, based upon his/her preferences. By simply applying display presentation filters to the image quality application, the reviewer could edit which data parameters would be displayed and in what fashion. While a QA specialist or departmental administrator performing a formal QA review may want to display all data inputs (which are time/date stamped and displayed using different color or other display schema), a radiologist tasked with interpreting a follow-up exam may only want to review the image quality data and image annotation of the preceding radiologist. The various data display presentation preferences can be automatically incorporated by the program 110 into individual end-users' profile, and can incorporate a number of variables including (but not limited to) exam type, anatomy, clinical indication, author of quality input data, and date/time of data entry.

A number of database analytics can be derived from the image quality database, including:
1. Stakeholder (technologist, radiologist, clinician)
2. Technology (model, age, upgrades)
3. Exam type (modality, anatomy)
4. Technical parameters (acquisition parameters, contrast administration)
5. Clinical data (clinical indication, medical/surgical history)
6. Imaging data (follow-up recommendations, report findings)
7. Patient profile (patient size, mobility, compliance)
8. Safety and economics (radiation dose, exam cost, iatrogenic complications)

The derived analytics can be created through manual or automated data queries. These quality analytics can be created in response to a specific event or concern (e.g., adverse, clinical outcome) or as a routine and periodic component of a continuous quality improvement program.

If, for example, a supervisory technologist or departmental administrator was notified of quality deficiencies for a particular technologist in the department, he/she may initiate a formal review of the technologist by retrieving and analyzing their image quality data over a defined time period, with or without specifications relating to the exam type, modality, clinical indication, or technology used. On the other hand, the same administrator may request routine (e.g., monthly) quality analyses for all technologists, along with an automated alert if any of these analytics identify quality ratings below a pre-determined threshold. In that situation, the program 110 would automatically create monthly reports on technologist quality performance. In the event that a pre-determined quality threshold was exceeded, a priority alert would be attached to the specific technologist report in question by the program 110, which would require receipt notification and acknowledgement by the administrator.

The extreme example of an adverse clinical outcome may have the program 110 mandate a formal institutional quality review of the patient's imaging folder, which would entail automated retrieval of all imaging quality data over the defined time course, and analysis of all imaging exams, stakeholders, and communications. This automated analysis is a far superior method for quality assessment compared to the current model requiring manual and time consuming review of non-standardized imaging data, which is often lacking in recorded quality data.

In addition to technical and clinical analysis of the quality database, technology assessment is an integral and highly valuable deliverable. Since the technology used is an essential component of the present invention, one can effectively perform a comparative technology assessment relating to image quality, while accounting for confounding variables such as patient profile, clinical indication, and technical parameters used in image acquisition. This would effectively create a technology quality scorecard, which provides consumers and technology producers with a data-driven methodology to compare the relative quality strengths and weaknesses of competing technologies. In the event that a technology is upgraded or refined, the same data analytics can be used by the program 110 to provide a "before and after" quality analysis, demonstrating the impact of the technology modification on quality metrics. If one was to incorporate data related to safety (e.g., radiation dose) and economics (e.g., technology purchase price and/or maintenance fees), the end result could be a multi-dimensional analysis of technology taking into account quality, safety, and cost.

The ability to input standardized quality data using multiple input options is another integral component of the program 110 of the present invention. The primary (but not necessarily only) forms of data input would include speech, graphical, and manual selection. All methods of data input would be directly linked by the program 110 to the quality ontology. Speech input would consist of using speech (voice) recognition technologies to incorporate standardized text into the imaging dataset. This could be as simple as highlighting the image of interest and speaking the quality data to be incorporated (e.g., motion artifact, high severity). If graphical data input was used, the end-user would input graphical data onto the selected image(s) through the use of an electronic stylus or tablet mapped to the image display device. In manual data input, the end-user would manually select the data from a computerized list of data elements, such as icons on a toolbar or text from a pull-down menu. The end product for all three forms of data input would be the same; standardized annotation and image mark-up of the selected "key" images, with the ability to display the corresponding text and numerical data by highlighting the annotation of interest.

In order to support this ability for multiple data input options, a QA Toolkit could be created by the program 110, which would provide icons and symbols on the computer toolbar, which are directly mapped to the quality ontology. Once an end-user becomes familiar with the standardized icons, symbols, and annotations used for image mark-up and data display, it would be anticipated that the need to refer to the corresponding textual format becomes minimized. This in effect creates a comprehensive and standardized image quality assessment (i.e., report), solely of the key image and associated graphical annotations.

The present invention includes a number of steps which are expanded below as follows.

In one embodiment, in customary use, the end-user signs into the program 110.

Figure 2A:
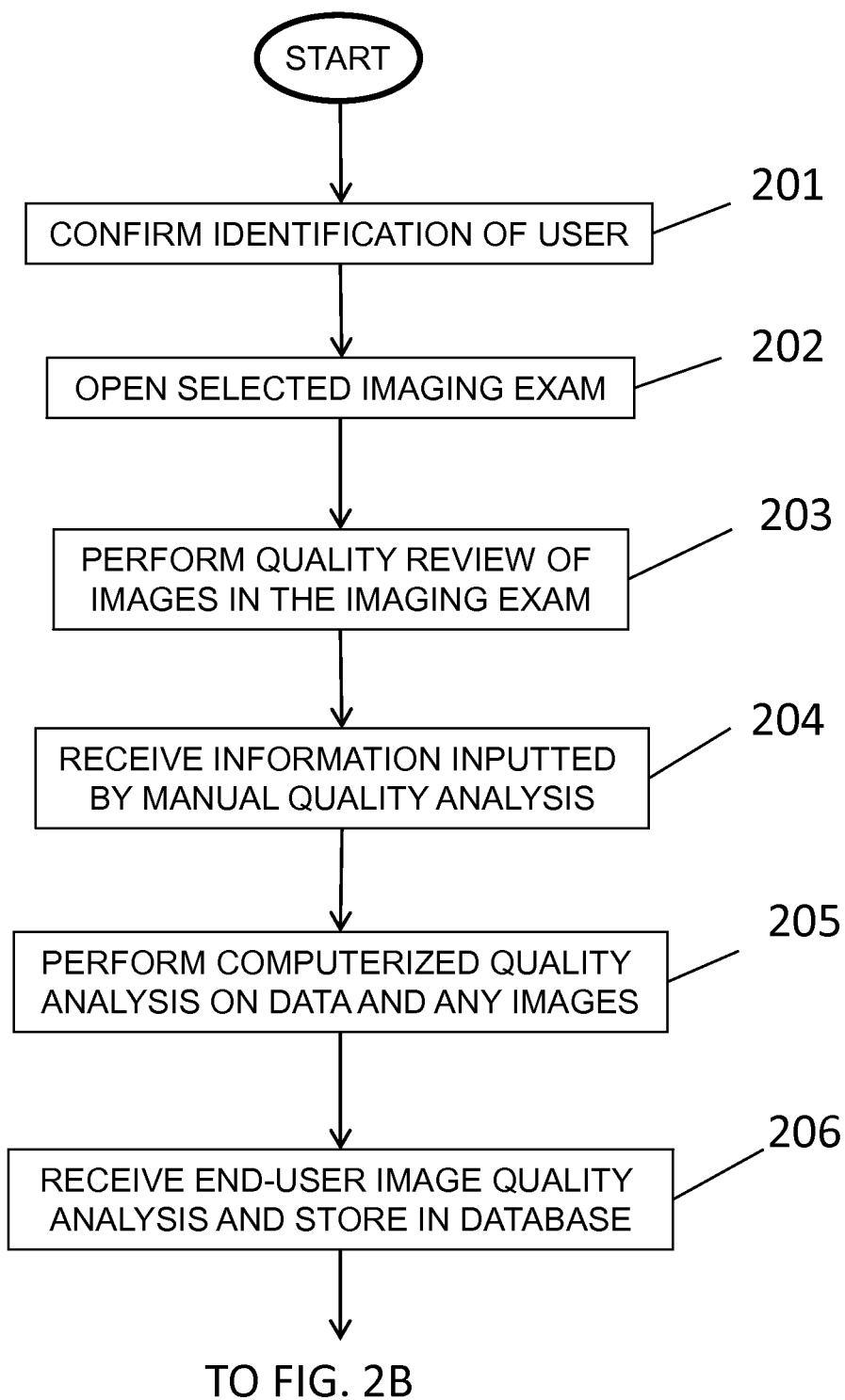

In step 201, the program 110 runs biometrics on the user to confirm identification, and perform authentication, of the user (see FIG. 2A).

Assuming that the biometrics confirms the user's credentials, in step 202, the program 110 will open the imaging exam that the user has indicated for review.

In step 203, the program 110 performs a quality review of the images in the image exam.

In step 204, the program 110 receives any information inputted by a manual quality analysis performed by the user.

In step 205, the program 110 performs a computerized quality analysis on the data and any images.

In step 206, the end-user reviews the imaging dataset and performs image quality analysis, which is stored in the database by the program 110.

In step 207, the program 110 saves data onto a key image (see FIG. 2B), using computer-generated standardized annotation and mark-up, or graphical data input (using table and stylus mapped to the image display device), or speech (using speech recognition), or using a computer toolbar used for the selection of icons and supporting data.

Variables recorded include comprehensive image quality (scale of 1-4), ability to render diagnosis (scale of 1-4, with 1 being "non-diagnostic", 2 being "limited", 3 being "diagnostic" and 4 being "exemplary"), specific quality deficiencies, and severity of each quality deficiency (scale of 1-4).

In step 208, the program 110 saves key images into the database.

In step 209, the user reviews the annotated images, and the program 110 accepts any edits from the user, and saves the annotated images in the database once complete.

In step 210, the finalized images and supporting data are transferred by the program 110 to QA database, such as the Patient Quality database, Technology Quality database, Exam-specific Quality database, or the Central Quality database, and linked to the original imaging dataset.

In step 211, the program 110 analyzes the image(s) and performs image quality analysis, In step 212, the program 110 selects key images and annotates them for quality deficiencies and supporting data based on the quality analysis.

In step 213, the program 110's provides its analysis of image quality to an authorized end-user (e.g., radiologist), for review.

In step 214, the End-user edits the computerized quality analysis mark-up and annotation, and the program 110 receives the edits, and the user's input to either: Accept as-is, Modify, or Reject.

In step 215, the program 110 receives an Accept input and saves the finalized image quality analysis with images and supporting data, in the Quality databases.

In one embodiment related to an Interactive Consultation Tool, the End-user reviews the imaging dataset and elects to initiate a consultation request with the program 110.

In step 301, the program 110 receives the user's selection of Key image(s) and displays same (see FIG. 3A).

In step 302, Image quality analysis is performed on the selected images by the program 110, using standardized annotation and mark-up.

In step 303, the program 110 invokes a consultation feature with supplemental text linked to the annotated image defining the question or requested action, and identification of the resulting consultant.

In step 304, the consultation protocol is initiated by the program 110 and the requested recipient of the consultation is electronically notified via a defined communication pathway (e.g., text, fax, instant messaging, email, etc.).

In step 305, the consultation request is electronically received and acknowledged by the consultant. If the consultation is accepted, the consultation file containing the annotated image(s) and text is transmitted to the consultant by the program 110. If the consultation request is denied, a rejection is electronically transmitted by the program 110 to the party requesting the consultation. All communications are recorded by the program 110 in the quality database.

In step 306, the consultant reviews the data and provides his analysis through free text and/or image annotation, which are stored in the quality imaging database by the program 110, along with the identity of the consultant and date/time of the data exchange.

In step 307, once completed, the consultant marks the consultation completed and the revised imaging data is transmitted back to the original party requesting the consultation, by the program 110 (see FIG. 3B).

In step 308, upon receipt, the original party reviews the recommendation and accompanying data, and the recipient is provided by the program 110 with the option of continuing the consultation, adding an additional party, or terminating it.

In step 309, all ensuing actions (including modification of the annotation/image mark-up, additional imaging, or modification of the imaging protocol) are recorded in the quality database by the program 110.

In one embodiment, with respect to data analytics (comparative technology assessment), the End-user (e.g., radiology administrator) requests manual query and analysis of the Image Quality Database.

In step 401, the program 110 reviews the credentials and authorization of the individual requesting the analysis, to ensure they have the proper authorization (defined by the institution) (see FIG. 4A).

In step 402, if authorization is verified, an acceptance is transmitted by the program 110 and the query is begun.

If rejected, a termination message is sent by the program 110 in step 403, and no further actions can be taken unless over-ridden by an authorized party.

In step 404, upon acceptance, the database analytics options are presented by the program 110 for selection by the end-user.

In step 405, the program 110 receives the administrator's selection, which in this case, is "Technology Assessment".

In step 406, the program 110 then requests the additional variables desired in the analysis, and the administrator selects the options for Imaging Modality (CT), All Exam Types, and All Patients. The Co-variables for Quality Analysis that can be selected include:
1. Patient profile (e.g., body habitus, morbidity, mobility, compliance)
2. Institutional profile (e.g., demographics, patient population served, geography, socio-economics)
3. Technology used (e.g., age, usage, upgrades, technical specifications)
4. Technical parameters (e.g., acquisition parameters, contrast administration, compensatory mechanisms (i.e., breath holding, change in pitch, exposure time))
5. Clinical data (e.g., medical/surgical history, clinical indication, supporting data (lab/pathology))
6. Imaging data (e.g., historical exams, prior report findings, previous image quality concerns)
7. Exam type (e.g., modality, protocol optimization, appropriateness)
8. Anatomy (e.g., organ system of interest, anatomic variation, prior surgery/radiation)
9. Safety parameters (e.g., radiation dose, contrast administration, iatrogenic complications)
10. Image processing (e.g., 2D/3D reconstructions, segmentation, smoothing/noise reduction)

In step 407, the scope of the search is requested by the program 110, and the administrator requests the option of Institutional Profile, no restrictions. This effectively requests a search of all institutions which have similar profiles to the host institution.

Figure 4B:
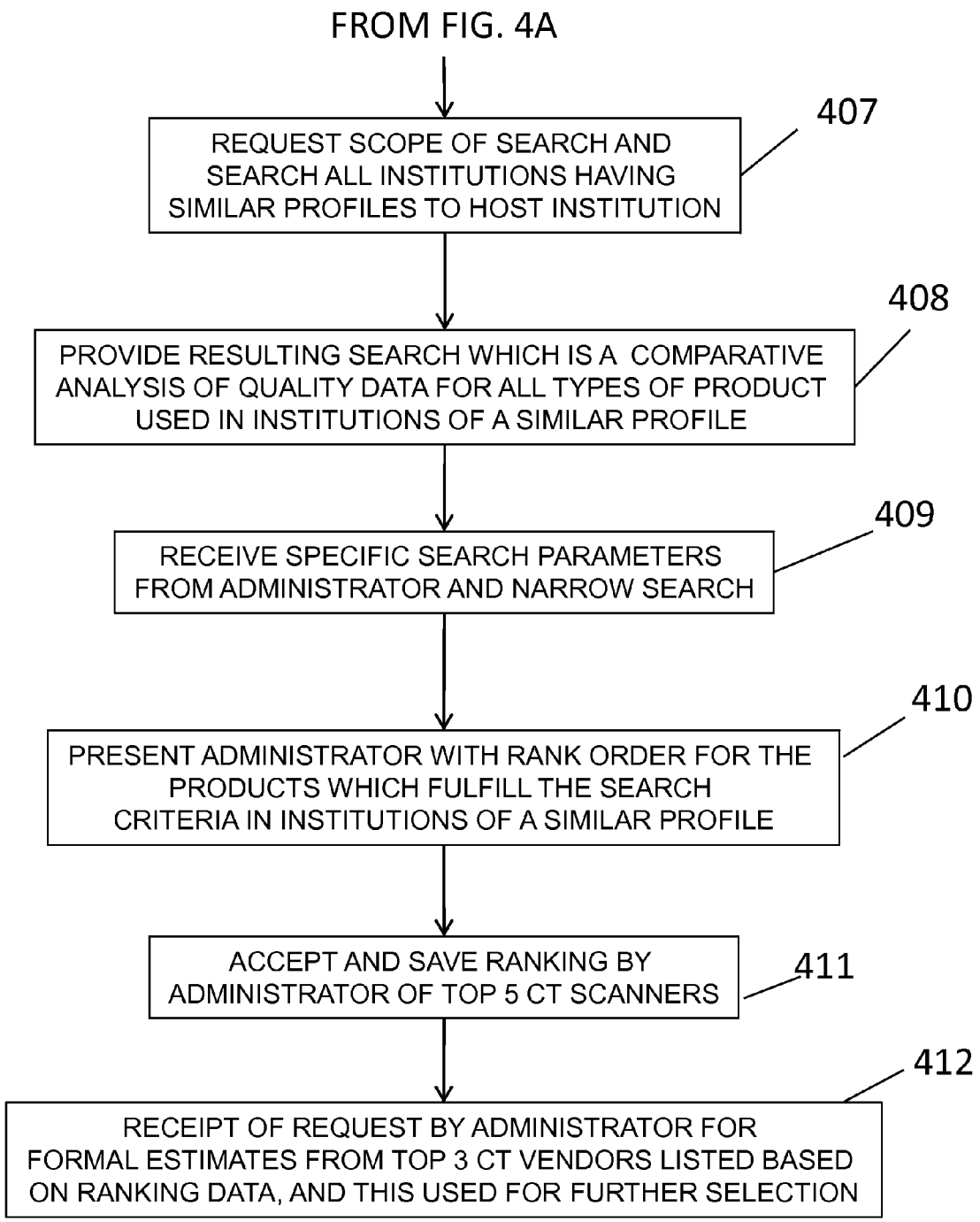

In step 408, the program 110 provides the resulting search, which is a comparative analysis of quality data for all types of CT scanners used in institutions of a similar profile (without restrictions on exam type or patient profiles) (see FIG. 4B).

In step 409, the administrator can then select specific search parameters of the various CT technologies in the analysis (e.g., age, manufacturer, cost, software packages), such that the program 110 can narrow its search.

In step 410, after narrowing the search criteria, the program 110 presents the administrator with a rank order (based upon quality metrics) for the different CT scanners which fulfill the search criteria in institutions of a similar profile.

In step 411, the administrator then elects to take the top 5 CT scanners (based upon comprehensive quality metrics) and then rank them according to manufacturer's recommended purchase price, which ranking is accepted and saved by the program 110.

In step 412, the administrator uses this ranking data to institute a request for formal estimates from the top 3 CT vendors listed (highest quality, lowest cost), which data is used for further selection.

In one embodiment, with respect to administrative review, the radiology administrator logs into the Quality database to perform quarterly technologist performance assessments, after authorization is verified by the program 110.

In step 501, the Administrator selects the query and search option, and selects "Technologist", and the program 110 retrieves all Technologists for display to the Administrator (see FIG. 5).

In step 502, the administrator inputs the name of the specific technologist for evaluation and defines the search criteria (i.e., quality metrics of interest, exam types, dates of search, modalities).

In step 503, the administrator then requests from the program 110, the population in which these quality measures will be compared (i.e., All Technologists within host institution).

In step 504, the program 110 provides the administrator with comparative statistics for the technologist in question relative to the other technologists in that department.

In step 505, if desired, the administrator can expand the search by the program 110, to include other criteria for the comparison data (e.g., education/training characteristics, clinical experience, institutional profile characteristics).

Figure 5B:
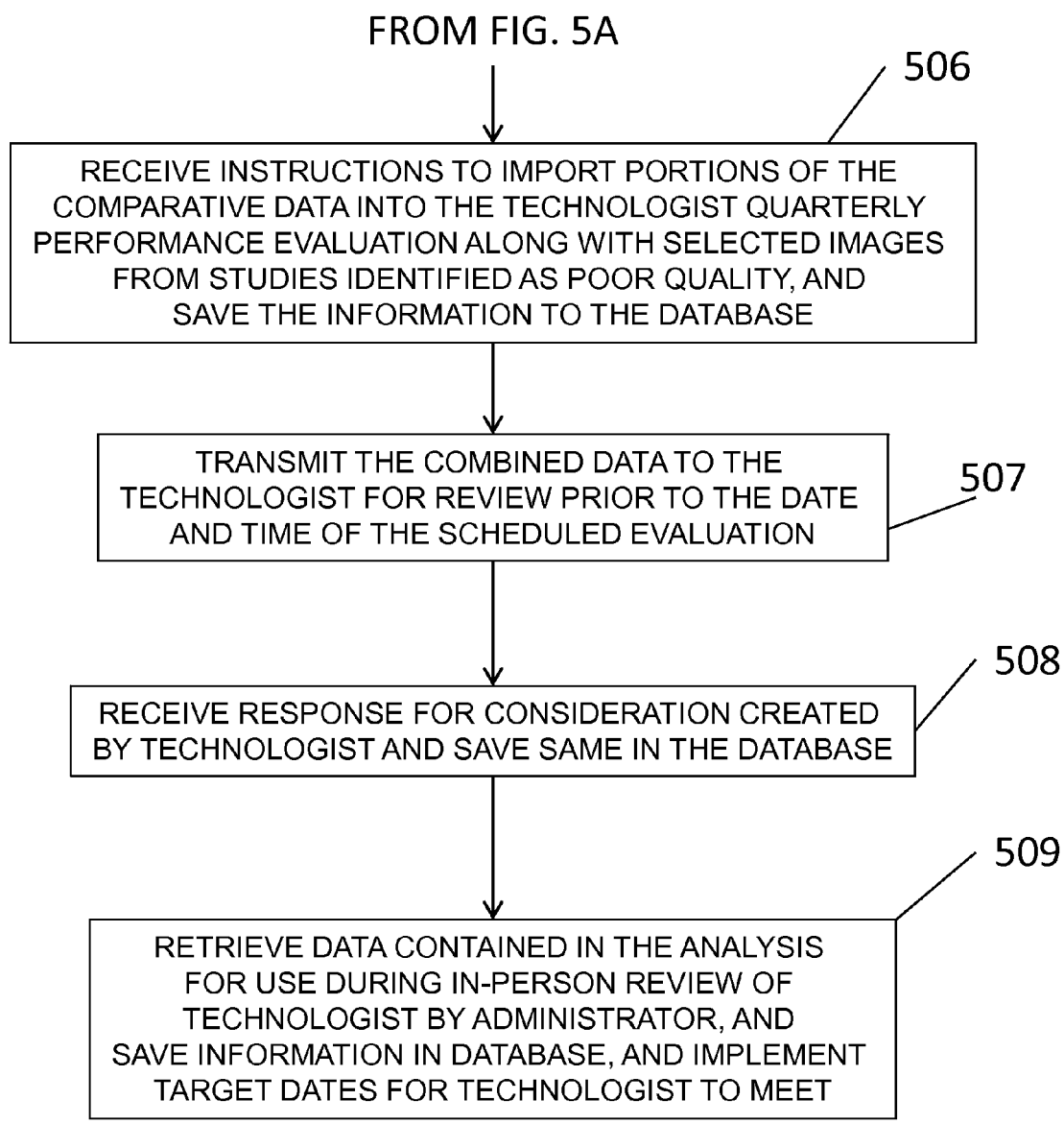

In step 506, the administrator then imports portions of this comparative data into the technologist quarterly performance evaluation along with selected images from studies identified as poor quality, and the program 110 saves the information to the database (see FIG. 5B).

In step 507, the combined data is transmitted by the program 110 to the technologist for review prior to the date and time of the scheduled evaluation.

In step 508, the technologist has the opportunity to review the data and associated "tagged" images prior to the meeting and create a response for consideration, which is saved in the database by the program 110.

In step 509, at the time of the in-person review with the Technologist, the data contained in the analysis is retrieved by the program 110 and reviewed by the Administrator and Technologist, and a plan is devised for targeted improvement and continued education, along with salary changes commensurate with the quality performance data. The program 110 saves this information and implements the target dates for the Technologist to meet.

In one embodiment, the program 110 allows for education and training of users, wherein if target or continued education dates for remedial action are not met, the program 110 will inform the appropriate authorities, and/or lock the Technologist out of the appropriate medical/Quality systems.

In one embodiment, the program 110 ensures that adverse clinical outcomes are analyzed, and a Root Cause Analysis can be made by the program 110 for any inputted adverse outcomes.

The present invention provides distinct advantages over conventional quality assurance systems, as shown in Table 1.

TABLE 1

Comparative Analysis of Conventional versus Proposed Quality Analysis

| Variable of Interest | Conventional QA | Proposed QA |
|---|---|---|
| Frequency of analysis | Occasional | Continuous |
| Case selection | Pre-selected | Randomized |
| Temporal analysis | Retrospective | Prospective |
| Evaluation process | External review | External + Internal review |
| Co-variables analyzed | Static | Dynamic |
| Database components | Non-standardized, text based | Standardized, image-centric |
| Education/training applications | Non-interactive database | Referenceable database with customizable filters and search |

Further, the present invention provides unique advantages and a wide array of advantages over conventional systems. These include:
1. Creation of a quality-centric ontology with the ability to map user preferred terms to a standardized quality nomenclature.
2. Creation of a standardized image annotation and mark-up system which maps to standardized text in the quality-centric ontology.
3. Creation of an image-based quality referenceable and searchable database which is categorized in accordance with standardized quality image annotation and ontology data elements.

4. Ability to incorporate new and existing societal and industry-wide quality standards into the quality metrics and analytics used and derived from the invention.

5. Correlation of clinical, patient, technology, institutional, and technical variables with derived image-based quality data for determination of interaction effects.

6. Creation of evidence-based best practice guidelines based upon meta-analysis of the standardized quality database and co-variables.

7. Ability to support both manual and automated data input for image quality assessment.

8. Ability to provide a mechanism for recording and tracking multi-user data input and editing.

9. Creation of a bi-directional quality consultation tool between different stakeholders (e.g., technologist-radiologist, radiologist-clinician, administrator-physicist).

10. Ability to integrate disparate technologies and data collection instruments into quality assessment data collection and analysis (e.g., computerized quality assessment, natural language processing (NLP), equipment quality control and radiation safety records).

11. Creation of a mechanism for randomized external quality data review and validation with targeted feedback and education.

12. Ability to perform anonymized real-time prospective image quality assessment.

13. Automated importation of image quality analysis data into radiology reports, with hypertext links to annotated images.

14. Continuous and dynamic recording and analysis of image quality data with ability to track quality analytics to individual end-user, patient, technology in use, exam type, and clinical data.

15. Ability to create automated quality data analytics in accordance with individual end-user preferences.

16. Creation of a customizable tool for automated quality alerts, based upon individual end-user preferences, criticality of the quality data and analytics, and institutional requirements.

17. Ability to create computer-based educational and training tools from the referenceable image quality database, to facilitate continuous quality improvement initiatives, educational in-services, and remedial training.

18. Ability to perform statistical analysis of the manual image quality analysis to correct for individual observer subjective bias, and provide "modified" quality data relative to the larger population of observers.

19. Creation of a technology assessment tool, which provides comparative quality analyses of various technology options.

20. Creation of an administrative analysis instrument which provides a mechanism to evaluate departmental and/or institutional quality performance relative to comparable peer performance data.

21. Creation of a computer-based QA toolkit which provides a customizable application for QA data input, retrieval, education, and analytics.

22. Utilization of the imaging quality database for real-time decision support.

23. The automated retrieval of all imaging quality data over the defined time course, and analysis of all imaging exams, stakeholders, and communications, to evaluate clinical outcomes.

24. The linkage of clinical data into the imaging quality database.

25. Clinical research made possible by the information stored in the quality database.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A computer-implemented method of performing image quality analysis of a plurality of images from an imaging examination, comprising:
    taking the plurality of images during the imaging examination of an individual using an imaging device, and recording the plurality of images in at least one database of a computer system;
    displaying the plurality of images from the imaging examination selected by a user, on a display of said computer system;
    performing a quality review of the plurality of images from said imaging examination, using a processor of said computer system;
    performing a quality analysis on data from said imaging examination and on the plurality of images using said processor;
    receiving image quality analysis on said data and said plurality of images and storing said image quality analysis in at least one database of said computer system;
    saving quality data from said image quality analysis on at least one key image of the plurality of images, using computer-generated standardized annotation and mark-up, graphical data input, textual, and numerical data elements, using a computerized tool of said computer system, and saving said quality data as annotated image data on said at least one key image, in said database; and
    transferring, using said processor, said annotated image data to at least one quality assurance database with linking to the plurality of images from the imaging examination.

2. The method of claim 1, further comprising:
    authenticating the user using biometrics.

3. The method of claim 1, further comprising:
    receiving any quality analysis information inputted by the user on the plurality of images, including speech data, in said quality review, to said at least one database.

4. The method of claim 1, wherein the user can review said annotated image data and can edit said annotated data prior to the processor transferring said saved annotated images to said at least one database.

5. The method of claim 1, wherein an image quality analysis is performed on said saved annotated image data by said processor.

6. The method of claim 5, wherein key images are selected and annotated for quality deficiencies and supporting data by said processor, based on said image quality analysis performed on said annotated image data.

7. The method of claim 4, further comprising:
    providing image quality analysis on said annotated image data, performed by said processor, to an authorized user for review.

8. The method of claim 7, wherein the authorized user edits said image quality analysis on said annotated image data, and said processor receives the authorized user's input to one of Accept as-is, Modify, or Reject said edits.

9. The method of claim 8, wherein on condition that an Accept as-is input is received by said processor, said edited image quality analysis with said annotated image data and supporting data, is saved in said at least one database.

10. The method of claim 1, further comprising:
initiating a consultation request with supplemental text linked to at least one annotated image in said annotated image data, defining a question or requested action, and identification of a consultant; and
providing a hierarchical rating as to a degree of timeliness and clinical significance associated with said consultation request.

11. The method of claim 10, further comprising:
notifying said consultant via electronic means of said consultation request; and
forwarding a consultation file containing said annotated image and text, including said image quality analysis, to said consultant when said consultant accepts said consultation request.

12. The method of claim 11, further comprising:
receiving a completed consultation from said consultant, with analysis and a revised annotated image from said consultant, and an identity of said consultant.

13. The method of claim 12, wherein the user has an option of continuing consultation with said consultant or an additional party or terminating consultation with said consultant.

14. The method of claim 13, further comprising:
recording all actions with said consultant in said at least one database.

15. The method of claim 1, further comprising:
providing database analytics, including a comparative analysis of quality data, to the user in ranked order.

16. The method of claim 1, further comprising:
providing comparative statistics to the user on personnel, and importing said comparative statistics into performance evaluations of said personnel, along with any supporting data.

17. The method of claim 16, further comprising:
devising a plan for targeted improvement and continued education of said personnel, along with salary changes commensurate with personnel quality performance data.

18. The method of claim 17, wherein when target or continued education dates for remedial action are not met by said personnel, said personnel are denied access to appropriate medical or Quality systems.

19. A computer system which performs image quality analysis of a plurality of images from an imaging examination, comprising:
at least one memory containing at least one program comprising the steps:
taking the plurality of images during the imaging examination of an individual using an imaging device, and recording the plurality of images in at least one database of a computer system;
displaying the plurality of images from the imaging examination selected by a user, on a display of said computer system;
performing a quality review of the plurality of images from said imaging examination, using a processor of said computer system;
performing a quality analysis on data from said imaging examination and on the plurality of images using said processor;
receiving image quality analysis on said data and said plurality of images and storing said image quality analysis in at least one database of said computer system;
saving quality data from said image quality analysis on at least one key image of the plurality of images, using computer-generated standardized annotation and mark-up, graphical data input, textual, and numerical data elements, using a computerized tool of said computer system, and saving said quality data as annotated image data on said at least one key image, in said database; and
transferring, using said processor, said annotated image data to at least one quality assurance database with linking to the plurality of images from the imaging examination; and
at least one processor for executing the program.

20. A non-transitory computer-readable medium whose contents cause a computer system to perform image quality analysis of a plurality of images from an imaging examination, the program comprising the steps of:
taking the plurality of images during the imaging examination of an individual using an imaging device, and recording the plurality of images in at least one database of a computer system;
displaying the plurality of images from the imaging examination selected by a user, on a display of said computer system;
performing a quality review of the plurality of images from said imaging examination, using a processor of said computer system;
performing a quality analysis on data from said imaging examination and on the plurality of images using said processor;
receiving image quality analysis on said data and said plurality of images and storing said image quality analysis in at least one database of said computer system;
saving quality data from said image quality analysis on at least one key image of the plurality of images, using computer-generated standardized annotation and mark-up, graphical data input, textual, and numerical data elements, using a computerized tool of said computer system, and saving said quality data as annotated image data on said at least one key image, in said database; and
transferring, using said processor, said annotated image data to at least one quality assurance database with linking to the plurality of images from the imaging examination.

21. The method of claim 1, wherein said quality data is used to create two simultaneous versions of report data, including said graphical, textual, and numerical data formats.

22. The method of claim 1, wherein said quality data can be viewed alone on said display, or viewed combined with radiology report data; and
wherein a combined report contains both radiologic findings and said image quality data, to determine how said imaging examination data was used for clinical diagnosis, as well as technical limitations in said clinical diagnosis due to image quality deficiencies.

23. The method of claim 22, wherein image quality deficiencies include a plurality of Quality Assessment Variables including: identifying information, exposure, positioning, spatial resolution, contrast resolution, radiation dose, noise, collimation, and artifacts.

24. The method of claim 1, further comprising:
instituting a secondary and external verification process of said imaging quality data which includes a second image quality analysis by an independent third party performed either in a blinded fashion or as an over-read having access to original data of said image quality analysis;
wherein in an event that a significant discrepancy exists between said image quality analysis and said secondary verification process of said image quality analysis, a final arbitrator is employed for anonymous reconciliation and finalization of said image quality analysis, without knowledge of a patient, operator, institutional, technology, or reviewer identity.

25. The method of claim 1, wherein color coding is used to distinguish between said quality data entered by different users; and
wherein filtering of quality data is provided such that only quality data of primary interest is displayed on said display to provide subjective preferences; and
wherein all quality data recorded in said database includes identification of the user, location, and time of an event.

26. The method of claim 10, wherein instead of said consultation request, a computerized search of said database is initiated to identify other annotated images with similar image quality deficiencies from multiple institutions, said annotated images which are combined and used for meta-analysis and search queries.

27. The method of claim 26, wherein annotated images of similar profiles are identified which present a match, while numerically rating a similarity between submitted images and said annotated images in said database of a similar appearance; and
wherein corresponding matched annotated images would then be available for review by a technologist along with supporting quality data including at least one of: technology used, image acquisition parameters, specific quality deficiency, clinical significance, or image quality score.

28. The method of claim 22, wherein when said image quality analysis shows that said annotated images are deficient in quality, additional or repeat imaging examination is required.

29. The method of claim 28, wherein said quality data is recorded in a stakeholder-specific database, which includes data related to quality metrics, education and training, and follow-up actions specific to each individual stakeholder.

30. The method of claim 28, wherein said quality data is recorded in an individual technology database to provide an objective measure for comparative technology assessment related to quality measures.

31. The method of claim 29, wherein said quality data is used prospectively to optimize work distribution, to maximize quality in accordance with historical quality analytics.

32. The method of claim 1, further comprising:
calculating an examination-specific patient quality assessment score, and attaching said patient quality assessment score to a request for said imaging examination.

33. The method of claim 32, further comprising:
matching a specific examination type, date, and said patient quality assessment score to an optimal technology and examination equipment operator.

34. The method of claim 1, further comprising:
associating said image quality data with historical imaging examinations to prospectively optimize image acquisition parameters to improve image quality and image examination safety.

35. The method of claim 1, wherein quality analytics are created through manual or automated data queries in response to a specific event or concern, or as a routine or periodic component of a continuous quality improvement program.

36. The method of claim 1, further comprising:
inputting a query and search of a database to retrieve a list of all technologists available, and displaying said list on a display of said computer system;
inputting a specific technologist on said list of technologists, for evaluation;
defining a search criteria in said database, of a specific population in which quality measures are compared;
analyzing, using said processor of said computer system, and displaying on said display, comparative statistics for said specific technologist relative to other technologists in a predefined department;
importing said comparative statistics into a quarterly performance evaluation of said specific technologist, along with selected of said plurality of images which do not meet a predefined quality threshold;
transmitting, by electronic means, combined data of said comparative statistics and said selected of said plurality of images, to said specific technologist for review prior to a date and time of a scheduled technologist performance assessment; and
reviewing said combined data and creating a response from said specific technologist for consideration by a reviewer.

37. The method of claim 36, wherein at a time of an in-person technology performance assessment with said specific technologist, said combined data contained in a said image quality analysis is retrieved from said database, reviewed by said reviewer and said technologist; and
wherein a plan is devised for targeted improvement and continued education for said specific technologist, along with salary changes commensurate with quality performance data, and target dates.

38. The method of claim 36, wherein said reviewer can expand said search to include other criteria for said comparison statistics, including at least one of education or training, clinical experience, or institutional profile.

* * * * *